US009669059B2

(12) United States Patent
Wang

(10) Patent No.: US 9,669,059 B2
(45) Date of Patent: Jun. 6, 2017

(54) BUTYROGENIC BACTERIA AS PROBIOTICS TO TREAT CLOSTRIDIUM DIFFICILE

(71) Applicant: University of Florida Research Foundation, Incorporated, Gainesville, FL (US)

(72) Inventor: Gary P. Wang, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 14/773,432

(22) PCT Filed: Mar. 9, 2014

(86) PCT No.: PCT/US2014/022207
§ 371 (c)(1),
(2) Date: Sep. 8, 2015

(87) PCT Pub. No.: WO2014/150094
PCT Pub. Date: Sep. 25, 2014

(65) Prior Publication Data
US 2016/0022745 A1    Jan. 28, 2016

Related U.S. Application Data

(60) Provisional application No. 61/793,704, filed on Mar. 15, 2013.

(51) Int. Cl.
| | |
|---|---|
| *C12R 1/00* | (2006.01) |
| *A61K 35/741* | (2015.01) |
| *A61K 35/74* | (2015.01) |
| *A61K 35/744* | (2015.01) |
| *C12Q 1/68* | (2006.01) |
| *A23L 33/135* | (2016.01) |
| *C12N 1/20* | (2006.01) |

(52) U.S. Cl.
CPC .......... *A61K 35/741* (2013.01); *A23L 33/135* (2016.08); *A61K 35/74* (2013.01); *A61K 35/744* (2013.01); *C12Q 1/689* (2013.01); *A23V 2002/00* (2013.01); *A23Y 2240/00* (2013.01); *C12N 1/20* (2013.01)

(58) Field of Classification Search
CPC ....................................................... C12R 1/00
See application file for complete search history.

(56) References Cited

U.S. PATENT DOCUMENTS

| | | | | |
|---|---|---|---|---|
| 5,443,826 | A | * | 8/1995 | Borody .................. A61K 35/74 424/543 |
| 2004/0028689 | A1 | | 2/2004 | Borody |
| 2006/0093592 | A1 | | 5/2006 | Cheruvanky et al. |
| 2008/0254009 | A1 | | 10/2008 | Finegold |

FOREIGN PATENT DOCUMENTS

WO    WO 2012/142605 A1    10/2012

OTHER PUBLICATIONS

Alonso, R. et al., "Rapid detection of toxigenic Clostridium difficile from stool samples by a nested PCR of toxin B gene," *J. Hosp. Infect.*, 1999, 41(2):145-149.
Ananthakrishnan, A., et al., "Clostridium difficile infection: epidemiology, risk factors and management," *Nat Rev Gastroenterol Hepatol*, 2011, 8(1):17-26.
Bäckhed, Fredrik et al., "The gut microbiota as an environmental factor that regulates fat storage," *Proc. Natl. Acad. Sci. U. S. A.*, 2004, 101:15718-15723.
Bakken, J.S., "Fecal bacteriotherapy for recurrent Clostridium difficile infection," *Anaerobe*, 2009, 15:285-289.
Berg, Rodney, "The indigenous gastrointestinal microflora." *Trends Microbiol*, 1996, 4:Abstract.
Bergey, D.H., et al., *Bergey's Manual of systematic bacteriology*, 1984, 1$^{st}$ edition, Williams & Wilkins, Baltimore, pp. 1-2.
Bergey, D.H., et al., *Bergey's manual of determinative bacteriology*, 1994, Williams & Wilkins, Baltimore, Abstract.
Bjorksten, B., et al., "Allergy development and the intestinal microflora during the first year of life," *J. Allergy Clin. Immunol.*, 2001, 108:516-520.
Boone, D.R., et al., *Bergey's Manual of systematic bacteriology*, Springer, New York, Abstract.
Borody, T.J., "Flora Power"—fecal bacteria cure chronic C. difficile diarrhea. *Am J Gastroenterol*, 2000, 95:3028-9.
Borriello, S.P., et al., "An in-vitro model of colonisation resistance to Clostridium difficile infection," *J. Med. Microbiol*, 1986, 21:299-309.
Brandt, L.J., et al., "Long-Term Follow-Up of Colonoscopic Fecal Microbiota Transplant for Recurrent Clostridium difficile Infection," *Am. J. Gastroenterol*, 2012, 107:1079-1087.
Cebra, John J. "Influences of microbiota on intestinal immune system development," *Am. J. Clin. Nutr.*, 1999, 69:1046S-1051S.
Chang, J.Y., et al., "Decreased diversity of the fecal Microbiome in recurrent Clostridium difficile—associated diarrhea," *J Infect Dis*, 2008, 197:435-8.
Claesson, M.J., et al., "Composition, variability, and temporal stability of the intestinal microbiota of the elderly," *Proc. Natl. Acad. Sci. U. S. A.* 108, 2011, Suppl 1:4586-4591.
Collins, M.D., et al., "The phylogeny of the genus *Clostridium*: proposal of five new genera and eleven new species combinations." *Int. J. Syst. Bacteriol.*, 1994, 44:812-826.
Cook, S.I., et al., "Review article: short chain fatty acids in health and disease," *Aliment. Pharmacol. Ther.*, 1998, 12:499-507.

(Continued)

*Primary Examiner* — Ruth Davis
(74) *Attorney, Agent, or Firm* — Saliwanchik, Lloyd & Eisenschenk

(57) ABSTRACT

The subject invention pertains to the use of certain bacterial strains, particularly butyrogenic bacteria, for preparing a composition to treat and/or prevent *Clostridium difficile* infection. In particular, the invention relates to the use of butyrate-producing anaerobic fermenters of gut commensals in pharmaceutical or food compositions.

6 Claims, 26 Drawing Sheets

(56) References Cited

OTHER PUBLICATIONS

Costello, E.K., et al., "Bacterial community variation in human body habitats across space and time," *Science*, 2009 326:1694-7.
Eckburg, P.B., et al., "Diversity of the human intestinal microbial flora," *Science*, 2005, 308:1635-8.
Famularo, G., et al., "Fecal bacteriotherapy or probiotics for the treatment of intestinal diseases?" *Am J Gastroenterol*, 2001, Abstract.
Frank, D.N., et al., "Molecular-phylogenetic characterization of microbial community imbalances in human inflammatory bowel diseases," *Proc. Natl. Acad. Sci. U. S. A.*, 2007, 104:13780-13785.
Goodman, A.L., et al., "Extensive personal human gut microbiota culture collections characterized and manipulated in gnotobiotic mice," *Proc. Natl. Acad. Sci. U. S. A.*, 2011, 108:6252-6257.
Guarner, Francisco, 2006. "Enteric flora in health and disease." Digestion 73 Suppl, 2006, 1:5-12.
Gumerlock, P.H., et al., "Use of the polymerase chain reaction for the specific and direct detection of Clostridium difficile in human feces," *Rev. Infect. Dis.*, 1991, 13:Abstract.
Hooper, L.V., et al., "How host-microbial interactions shape the nutrient environment of the mammalian intestine." *Annu. Rev. Nutr.*, 2002, 22:283-307.
Johnson, J.L., et al., "Taxonomy of the Clostridia: ribosomal ribonucleic acid homologies among the species," *J. Gen. Microbiol.* 1975, 88:229-244.
Kato, N., et al., "Detection of toxigenic Clostridium difficile in stool specimens by the polymerase chain reaction," *J Infect Dis*, 1993, 167:Abstract.
Kuhl, S.J., et al., "Diagnosis and monitoring of Clostridium difficile infections with the polymerase chain reaction," *Clin Infect Dis*, 1993, 16 Suppl 4:S234-8.
Lee, Y.J., et al., "Identification and screening for antimicrobial activity against Clostridium difficile of *Bifidobacterium* and *Lactobacillus* species isolated from healthy infant faeces," *Int J Antimicrob Agents*, 2003, 21:Abtract.
Lozupone, C., et al., "UniFrac: an effective distance metric for microbial community comparison," *Isme J.*, 2011, 5:169-172.
Marra, F., et al., "Does antibiotic exposure during infancy lead to development of asthma? A systematic review and metaanalysis," 2006. Chest 136:e30.
Naaber, P., et al., "Inhibition of Clostridium difficile strains by intestinal *Lactobacillus* species," *J Med Microbiol*, 2004, 53:551-4.
Noverr, M.C., et al., "The 'microflora hypothesis' of allergic diseases," *Clin. Exp. Allergy*, 2005, 35:1511-1520.
O'Keefe, S.J., "Tube feeding, the microbiota, and Clostridium difficile infection," *World J Gastroenterol*, 2010, 16:139-42.
Parkes, G.C., et al., "The mechanisms and efficacy of probiotics in the prevention of Clostridium difficile-associated diarrhea," *Lancet Infect Dis*, 2009, 9:Abstract.
Pavlidis, P., et al., "Matrix2png: a utility for visualizing matrix data," *Bioinformatics*, 2003, 19:295-296.
Pépin, J., et al., "Increasing risk of relapse after treatment of Clostridium difficile colitis in Quebec, Canada," *Clin. Infect. Dis.*, 2005, 40:1591-1597.
Petrella, L.A., et al., "Decreased Cure and Increased Recurrence Rates for Clostridium difficile Infection Caused by the Epidemic C. difficile BI Strain," *Clin. Infect. Dis.*, 2012, 55:351-357.
Prioult, G., et al., "Mucosal immunity and allergic responses: lack of regulation and/or lack of microbial stimulation?" *Immunol. Rev.*, 2005, 206:Abstract.
Pruesse, E., et al., "SILVA: a comprehensive online resource for quality checked and aligned ribosomal RNA sequence data compatible with ARB," *Nucleic Acids Res*, 2007, 35:7188-96.
Reeves, A.E., et al., "Suppression of Clostridium difficile in the Gastrointestinal Tract of Germ-Free Mice Inoculated with a Murine Lachnospiraceae Isolate.," *Infect. Immun.*, 2012.
Rolfe, R.D., "Bacterial interference between Clostridium difficile and normal fecal flora," *J. Infect. Dis.*, 1981, 143:Abstract.
Russell, G., "Fecal bacteriotherapy for relapsing Clostridium difficile infection in a child: a proposed treatment protocol," Pediatrics, 2010, 126:Abstract.
Salonen, A., et al., "Comparative analysis of fecal DNA extraction methods with phylogenetic microarray: effective recovery of bacterial and archael DNA using mechanical cell lysis," *J Microbial Methods*, 2010, 81:127-34.
Segata, N., et al., "Metagenomic biomarker discovery and explanation," *Genome Biol.*, 2011, 12:R60.
Wilson, K.H., et al., "The microecology of Clostridium difficile," *Clin. Infect. Dis.*, 1993, 16 Suppl 4:Abstract.
Wilson, K.H., et al., "Interaction of *Clostridium difficile* and *Escherichia coli* with microfloras in continuous-flow cultures and gnotobiotic mice," *Infect Immun*, 1986, 54:354-8.
Wong, J.M., et al., "Colonic health: fermentation and short chain fatty acids," *J. Clin. Gastroenterol.*, 2006, 40:Abstract.
Wu, G.D., et al., "Sampling and pyrosequencing methods for characterizing bacterial communities in the human gut using 16S sequence tags," *BMC Microbiol*, 2010, 10:206.
Young, V.B., "Overview of the gastrointestinal microbiota," *Adv. Exp. Med. Biol.*, 2008, 635:29-40.

* cited by examiner

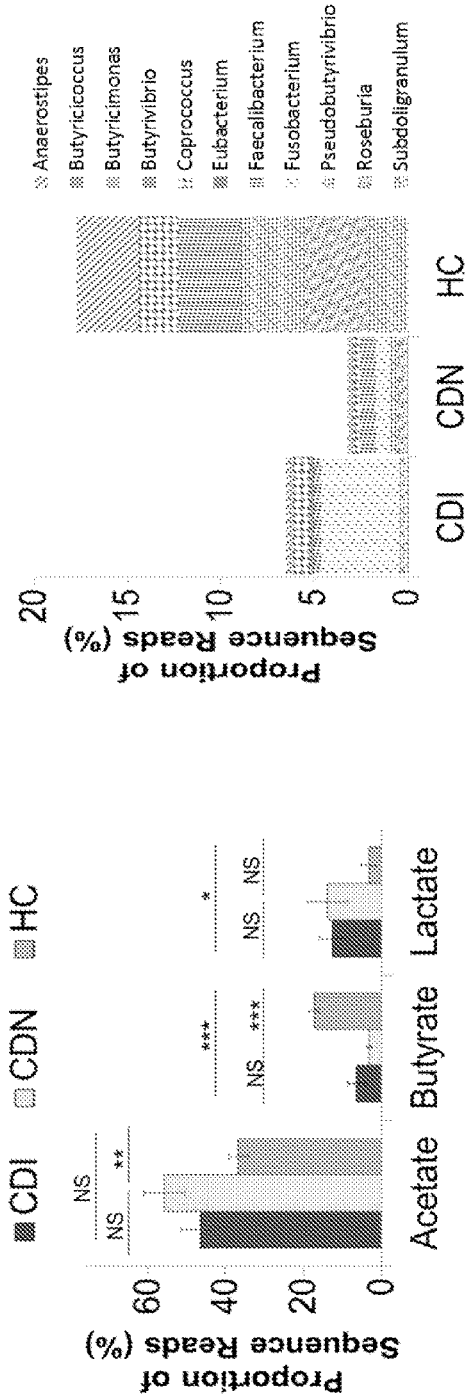
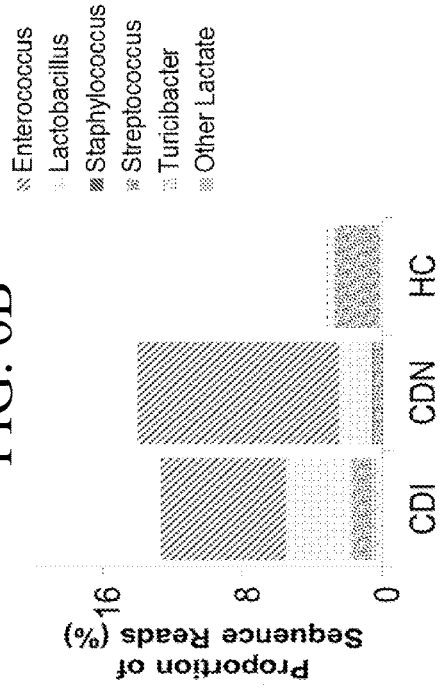
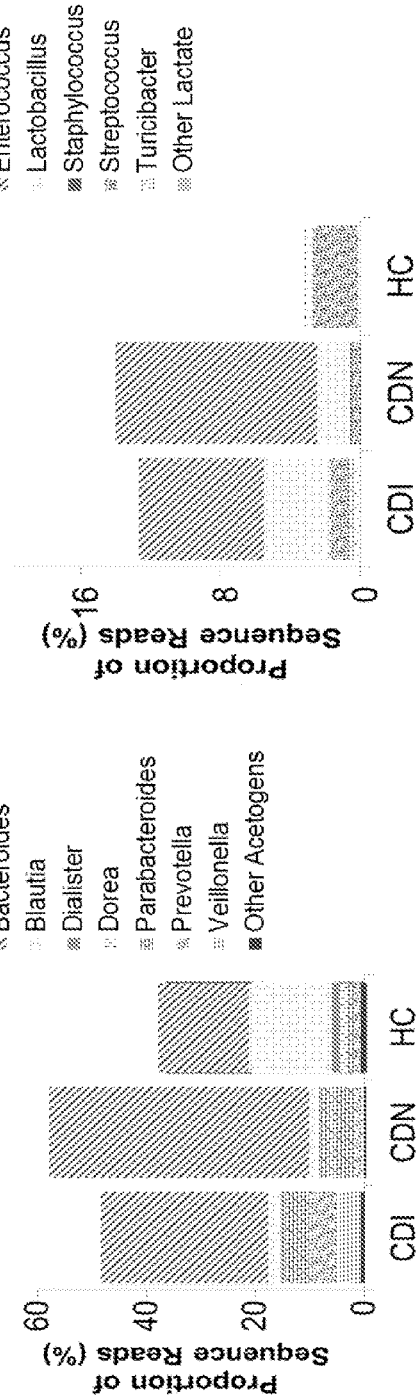
FIG. 6A  FIG. 6B  FIG. 6C  FIG. 6D

- Actinobacteria
- Bacteroides
- Firmicutes
- Fusobacteria
- Proteobacteria
- Synergistetes
- Tenericutes
- Verrucomicrobia

| Pool 1 | BC | Description | Final Read Count after Quality Control | % Retained |
|---|---|---|---|---|
| H.1 | ACTCTACT | healthy | 9947 | 87% |
| CDP.1 | AGACAGCT | C.diff.pos | 6236 | 87% |
| H.2 | ACTCGCGT | healthy | 5984 | 90% |
| CDP.2 | AGAGACGT | C.diff.pos | 4942 | 88% |
| CDP.3 | AGTCTAGC | C.diff.pos | 4606 | 87% |
| CDN.1 | CGTCATAG | C.diff.neg | 3758 | 77% |
| H.3 | ACTGTGAT | healthy | 3968 | 82% |
| CDP.4 | AGTGACTG | C.diff.pos | 4236 | 91% |
| H.4 | ACTGCAGA | healthy | 4095 | 91% |
| CDP.5 | TCACATGC | C.diff.pos | 3876 | 87% |
| CDP.6 | AGAGTCAG | C.diff.pos | 3642 | 88% |
| CDP.7 | AGTAGCAC | C.diff.pos | 3210 | 78% |
| CDP.8 | TCACTACG | C.diff.pos | 3642 | 90% |
| H.5 | TCGTCAGT | healthy | 3428 | 91% |
| H.6 | TCGACTCT | healthy | 3214 | 88% |
| CDP.9 | TCTAGTGC | C.diff.pos | 3097 | 87% |
| CDP.10 | ACTCGTAG | C.diff.pos | 3017 | 86% |
| CDP.11 | TCATGTCG | C.diff.pos | 3126 | 90% |
| H.7 | ACTATCTG | healthy | 2817 | 85% |

| Pool 2 | BC | Description | Final Read Count after Quality Control | % Retained |
|---|---|---|---|---|
| H.8 | ACTGCTAT | healthy | 10158 | 88% |
| H.9 | ACTATGTG | healthy | 6068 | 86% |
| H.10 | TGTGCTCT | healthy | 5755 | 86% |
| CDN.2 | CGTGACAT | C.diff.neg | 5845 | 89% |
| H.11 | AGACACAT | healthy | 5417 | 89% |
| WCDP.12 | TGAGTGCT | weak.C.diff.pos | 4404 | 88% |
| H.12 | TGTCGTAC | healthy | 4249 | 87% |
| H.13 | ACTCGAGA | healthy | 4241 | 91% |
| H.14 | ACTCTGCT | healthy | 3975 | 88% |
| CDP.13 | AGACATGA | C.diff.pos | 3748 | 86% |
| CDP.14 | TCTGTAGC | C.diff.pos | 3417 | 88% |
| H.15 | TCGTACTG | healthy | 3202 | 86% |
| CDP.15 | TATCGACG | C.diff.pos | 2971 | 90% |
| H.16 | ACTGTCGT | healthy | 2996 | 91% |
| CDP.16 | TCTCTCAG | C.diff.pos | 2719 | 83% |
| CDP.17 | AGAGCTGT | C.diff.pos | 2811 | 90% |
| H.17 | ACTATCAC | healthy | 2579 | 85% |
| CDP.18 | TCTGATCG | C.diff.pos | 2194 | 85% |
| CDP.19 | TCTCACTC | C.diff.pos | 1862 | 84% |
| CDP.20 | TAGACGAC | C.diff.pos | 1750 | 88% |

| Pool 3 | BC | Description | Final Read Count after Quality Control | % Retained |
|---|---|---|---|---|
| CDN.3 | CGATATCG | C.diff.neg | 7640 | 91% |
| H.18 | ACTCGTGT | healthy | 7361 | 90% |
| H.19 | TCGTCTAC | healthy | 6732 | 90% |
| CDP.21 | TGACGTCT | C.diff.pos | 6380 | 92% |
| CDP.22 | TCTCTGCT | C.diff.pos | 6238 | 91% |
| H.20 | TGTGTCAC | healthy | 5798 | 89% |

FIG. 14A

| | | | | |
|---|---|---|---|---|
| CDP.23 | ATCTGCTC | C.diff.pos | 5720 | 89% |
| CDP.24 | AGCTCTAC | C.diff.pos | 5752 | 91% |
| CDP.25 | AGAGACAT | C.diff.pos | 5451 | 90% |
| H.21 | ACTCACAT | healthy | 5147 | 89% |
| H.22 | TCGAGTAG | healthy | 4937 | 92% |
| H.23 | TGTCTGTC | healthy | 4585 | 89% |
| CDN.4 | ACTCTGAC | C.diff.neg | 4419 | 92% |
| H.24 | TCAGACGT | healthy | 3807 | 89% |
| CDP.26 | AGACGATA | C.diff.pos | 3757 | 94% |
| CDP.27 | TATCTCGC | C.diff.pos | 3649 | 92% |
| CDP.28 | TAGAGAGC | C.diff.pos | 3375 | 89% |
| CDP.29 | TCACGATC | C.diff.pos | 3152 | 91% |
| CDN.5 | CTCGTATC | C.diff.neg | 2682 | 91% |
| Pool 4 | BC | Description | Final Read Count after Quality Control | % Retained |
| CDN.6 | AGATCGCA | C.diff.neg | 8980 | 86% |
| H.25 | TGTGCATG | healthy | 8023 | 90% |
| CDP.30 | AGCACAGT | C.diff.pos | 7669 | 88% |
| H.26 | ACTCTCAT | healthy | 7307 | 90% |
| CDN.7 | CGATCATG | C.diff.neg | 7252 | 92% |
| H.27 | ACTCAGTA | healthy | 7004 | 91% |
| H.28 | AGACACGT | healthy | 6253 | 90% |
| H.29 | TGATCTGC | healthy | 5739 | 90% |
| H.30 | ACTGTGCT | healthy | 4578 | 86% |
| CDP.31 | AGTCGTGT | C.diff.pos | 4789 | 93% |
| CDN.8 | CGTACACT | C.diff.neg | 4179 | 86% |
| CDP.32 | TCTGCGAT | C.diff.pos | 4350 | 91% |
| CDN.9 | ACGATGTG | C.diff.neg | 4211 | 91% |
| CDP.33 | AGCTACAG | C.diff.pos | 3941 | 90% |
| H.31 | TCGATCAC | healthy | 3629 | 90% |
| CDP.34 | TAGTGCGT | C.diff.pos | 3337 | 86% |
| CDN.10 | CGTCTGAT | C.diff.neg | 3069 | 82% |
| Pool 5 | BC | Description | Final Read Count after Quality Control | % Retained |
| H.32 | ACTGCTGT | healthy | 7864 | 88% |
| H.33 | ACTCTCGT | healthy | 7120 | 88% |
| H.34 | ACTAGCGA | healthy | 6769 | 89% |
| H.35 | ACTGTACT | healthy | 6317 | 86% |
| H.36 | ACTGACAT | healthy | 5982 | 90% |
| CDP.35 | TCATGCAC | C.diff.pos | 5786 | 90% |
| H.37 | ACTGAGTA | healthy | 5217 | 92% |
| CDN.11 | CTGTCACT | C.diff.neg | 4906 | 91% |
| CDN.12 | CTGCATCT | C.diff.neg | 4631 | 91% |
| CDN.13 | CGTATCAG | C.diff.neg | 4454 | 90% |
| CDP.36 | AGACTCAT | C.diff.pos | 4472 | 91% |
| CDN.14 | CTGTGATC | C.diff.neg | 4196 | 91% |
| CDP.37 | TGCTACTC | C.diff.pos | 3956 | 88% |
| CDN.15 | CTGTCTAG | C.diff.neg | 4062 | 92% |
| CDN.16 | CGATGTAC | C.diff.neg | 3992 | 91% |
| CDN.17 | CTGATGTC | C.diff.neg | 3950 | 90% |
| CDP.38 | AGACTGTA | C.diff.pos | 3890 | 90% |
| CDP.39 | TCATCGTG | C.diff.pos | 3875 | 94% |
| H.38 | TGTAGCTG | healthy | 3442 | 89% |
| CDN.18 | CTGCTATG | C.diff.neg | 3008 | 81% |
| CDN.19 | ACGACGAT | C.diff.neg | 3074 | 91% |

FIG. 14B

| Pool 6 | BC | Description | Final Read Count after Quality Control | % Retained |
|---|---|---|---|---|
| H.39 | ACTCTGAT | healthy | 9106 | 91% |
| CDN.20 | AGATAGTG | C.diff.neg | 7046 | 90% |
| CDN.21 | TGCGATAC | C.diff.neg | 6531 | 90% |
| CDN.22 | TGCTCGAT | C.diff.neg | 6129 | 90% |
| CDN.23 | TGCAGACT | C.diff.neg | 5635 | 90% |
| CDN.24 | ACGAGAGT | C.diff.neg | 5667 | 92% |
| CDN.25 | ACGTCATC | C.diff.neg | 5533 | 91% |
| CDN.26 | TGCATAGC | C.diff.neg | 5491 | 90% |
| CDN.27 | ACTCAGTG | C.diff.neg | 5188 | 90% |
| CDN.28 | TGCATGTG | C.diff.neg | 5109 | 90% |
| CDN.29 | TGACAGTG | C.diff.neg | 4338 | 90% |
| H.40 | ACTGTCAT | healthy | 4283 | 91% |
| CDN.30 | ACTATCGC | C.diff.neg | 4247 | 90% |
| CDN.31 | ATAGCGTC | C.diff.neg | 4125 | 90% |
| CDN.32 | ACTGCTAC | C.diff.neg | 4166 | 92% |
| CDN.33 | ACGTGTCT | C.diff.neg | 3565 | 81% |
| CDN.34 | ATCGATGC | C.diff.neg | 3667 | 90% |
| CDN.35 | ACGTATGC | C.diff.neg | 3570 | 91% |
| CDN.36 | AGTACTCG | C.diff.neg | 3170 | 92% |

FIG. 14C

| Genera | CDI | HC | p-value | Classification | Significance |
|---|---|---|---|---|---|
| Bacteroides | 29.54% | 16.12% | 1.06E-02 | A | · |
| Blautia | 2.14% | 14.45% | 3.67E-12 | A | · |
| Roseburia | 0.17% | 3.37% | 3.19E-10 | B | · |
| Pseudobutyrivibrio | 0.07% | 3.27% | 4.82E-06 | B | · |
| Faecalibacterium | 0.37% | 3.25% | 5.40E-06 | B | · |
| Anaerostipes | 0.20% | 3.10% | 1.04E-04 | B | · |
| Streptococcus | 1.01% | 2.52% | 4.18E-01 | L | |
| Subdoligranulum | 0.18% | 2.05% | 1.81E-06 | B | · |
| Coprococcus | 0.94% | 2.02% | 5.69E-02 | B | |
| Alistipes | 4.39% | 1.81% | 2.86E-01 | S | |
| Ruminococcus | 0.26% | 1.70% | 1.67E-04 | mixed | · |
| Dorea | 0.12% | 1.55% | 7.17E-08 | A | · |
| Akkermansia | 2.66% | 1.53% | 4.07E-01 | U | |
| Dialister | 0.48% | 1.40% | 2.79E-01 | A | |
| Prevotella | 4.20% | 1.19% | 1.78E-01 | A | |
| Parabacteroides | 4.69% | 1.02% | 4.24E-02 | A | · |
| Collinsella | 0.03% | 0.83% | 9.94E-06 | mixed | · |
| Clostridium | 2.98% | 0.78% | 1.15E-01 | mixed | |
| Barnesiella | 0.07% | 0.65% | 6.71E-03 | trace A, S | · |
| Catenibacterium | 0.03% | 0.57% | 3.17E-02 | U | · |
| Phascolarctobacterium | 0.34% | 0.52% | 3.32E-01 | S | |
| Lactobacillus | 3.71% | 0.45% | 3.55E-02 | L | · |
| Anaerotruncus | 0.16% | 0.43% | 3.07E-02 | A,B | · |
| Paraprevotella | 0.15% | 0.25% | 4.59E-01 | A | |
| Lachnospira | 0.03% | 0.24% | 9.18E-04 | A | · |
| Marvinbryantia | 0.00% | 0.20% | 1.73E-04 | A | · |
| Parasutterella | 0.10% | 0.16% | 6.17E-01 | U | |
| RC9 gut group | 0.00% | 0.14% | 1.83E-01 | U | |
| Thalassospira | 0.00% | 0.11% | 7.86E-02 | U | |
| Megasphaera | 0.02% | 0.11% | 3.65E-01 | U | |
| Flavonifractor | 0.43% | 0.11% | 7.56E-02 | U | |
| Escherichia-Shigella | 0.50% | 0.08% | 4.35E-02 | U | · |
| Turicibacter | 0.69% | 0.07% | 3.63E-01 | L | |
| Acidaminococcus | 0.01% | 0.07% | 4.25E-02 | A, B | · |

FIG. 15A

| | | | | |
|---|---|---|---|---|
| Butyricimonas | 0.15% | 0.05% | 2.17E-01 | B |
| Enterococcus | 7.07% | 0.05% | 2.15E-02 | L |
| Adlercreutzia | 0.00% | 0.05% | 3.37E-04 | Equol |
| Cloacibacillus | 0.22% | 0.05% | 4.32E-01 | A,B |
| Mogibacterium | 0.00% | 0.04% | 2.48E-01 | Phenyl acetate |
| Sutterella | 2.33% | 0.04% | 1.52E-01 | S |
| Slackia | 0.00% | 0.04% | 2.99E-02 | U |
| Lactococcus | 0.01% | 0.03% | 3.90E-01 | L |
| Desulfovibrio | 0.01% | 0.03% | 5.58E-02 | U |
| Bilophila | 0.02% | 0.03% | 5.20E-01 | A |
| Eggerthella | 0.03% | 0.03% | 7.97E-01 | U |
| Fusobacterium | 4.08% | 0.03% | 9.88E-02 | B |
| Holdemania | 0.01% | 0.02% | 8.65E-03 | A |
| Sarcina | 0.00% | 0.02% | 4.48E-02 | U |
| Moryella | 0.04% | 0.02% | 5.91E-01 | A,B,L |
| Eubacterium | 0.15% | 0.02% | 2.55E-01 | B |
| Howardella | 0.01% | 0.02% | 2.53E-01 | U |
| Allisonella | 0.00% | 0.01% | 1.91E-01 | Histamine |
| Christensenella | 0.00% | 0.01% | 3.64E-02 | A |
| Gordonibacter | 0.00% | 0.01% | 6.97E-02 | U |
| Enterobacter | 0.23% | 0.01% | 1.17E-01 | U |
| drogenoanaerobacterium | 0.00% | 0.01% | 1.75E-01 | Hydrogen |
| Oscillibacter | 0.00% | 0.01% | 1.49E-01 | V |
| Citrobacter | 0.47% | 0.01% | 1.98E-01 | U |
| Oxalobacter | 0.00% | 0.01% | 3.34E-02 | F |
| Butyrivibrio | 0.00% | 0.01% | 6.91E-02 | B |
| Megamonas | 0.00% | 0.01% | 2.50E-01 | U |
| Weissella | 0.00% | 0.01% | 2.55E-01 | L |
| Shuttleworthia | 0.00% | 0.01% | 1.04E-02 | A,B |
| Actinomyces | 0.16% | 0.01% | 1.39E-01 | A |
| Anaerofilum | 0.00% | 0.005% | 4.45E-02 | A |
| Pseudoflavonifractor | 0.00% | 0.005% | 9.54E-01 | A |
| Enterorhabdus | 0.00% | 0.005% | 1.21E-01 | U |
| Gelria | 0.00% | 0.004% | 5.77E-02 | P,S |
| Solobacterium | 0.05% | 0.004% | 2.92E-01 | U |
| Anaeroplasma | 0.00% | 0.004% | 3.23E-01 | A |
| Parvimonas | 0.01% | 0.004% | 3.06E-01 | A |
| Peptostreptococcus | 0.01% | 0.004% | 5.24E-01 | U |
| Acetanaerobacterium | 0.00% | 0.003% | 4.68E-01 | A |
| Granulicatella | 0.03% | 0.003% | 3.22E-02 | U |
| Leuconostoc | 0.01% | 0.003% | 3.17E-01 | A |
| Rothia | 0.03% | 0.003% | 1.62E-01 | U |
| Papillibacter | 0.00% | 0.003% | 2.05E-01 | Cinnamate |

FIG. 15B

| | | | | |
|---|---|---|---|---|
| Porphyromonas | 0.12% | 0.003% | 3.00E-01 | U |
| Corynebacterium_1 | 0.01% | 0.003% | 5.21E-01 | L,S |
| Campylobacter | 0.10% | 0.002% | 1.75E-01 | U |
| Victivallis | 0.00% | 0.002% | 6.87E-01 | A |
| Asteroleplasma | 0.00% | 0.002% | 3.23E-01 | A |
| Atopobium | 0.04% | 0.002% | 9.10E-02 | A |
| Anaerofustis | 0.00% | 0.002% | 2.92E-01 | A,B |
| Peptoniphilus | 0.13% | 0.002% | 1.46E-01 | U |
| Acetitomaculum | 0.00% | 0.002% | 3.23E-01 | A |
| Gemella | 0.02% | 0.002% | 3.33E-01 | A |
| Corynebacterium_4 | 0.00% | 0.001% | 1.62E-01 | L,S |
| Coprobacillus | 0.00% | 0.001% | 3.23E-01 | U |
| Selenomonas | 0.01% | 0.001% | 1.50E-01 | U |
| Staphylococcus | 0.02% | 0.001% | 2.32E-02 | L |
| Desulfobulbus | 0.00% | 0.001% | 3.23E-01 | A |
| Leptotrichia | 0.00% | 0.001% | 2.77E-01 | U |
| Aerococcus | 0.00% | 0.001% | 3.23E-01 | U |
| Tannerella | 0.00% | 0.001% | 4.33E-01 | A,B |
| Oribacterium | 0.00% | 0.001% | 4.96E-01 | A |
| Dysgonomonas | 1.16% | 0.001% | 2.74E-01 | P,L,S |
| Pantoea | 0.00% | 0.0005% | 9.44E-01 | U |
| Butyricicoccus | 0.00% | 0.0005% | 3.23E-01 | B |
| Eikenella | 0.08% | 0.0003% | 1.05E-01 | U |
| Anaeroglobus | 0.00% | 0.0003% | 6.50E-01 | A,B |
| Anaerosporobacter | 0.02% | 0.00% | 2.68E-01 | A |
| Cellulosilyticum | 0.02% | 0.00% | 3.24E-01 | A |
| Lutispora | 0.002% | 0.00% | 3.24E-01 | A |
| Pyramidobacter | 0.03% | 0.00% | 3.24E-01 | A |
| Robinsoniella | 0.09% | 0.00% | 1.69E-01 | A |
| Xylanibacter | 0.001% | 0.00% | 3.24E-01 | A |
| Aggregatibacter | 0.001% | 0.00% | 1.61E-01 | U |
| Allobaculum | 0.001% | 0.00% | 3.24E-01 | U |
| Balneimonas | 0.001% | 0.00% | 3.24E-01 | U |
| Brevibacterium | 0.003% | 0.00% | 1.84E-01 | U |
| Cardiobacterium | 0.0005% | 0.00% | 3.24E-01 | U |
| Dermabacter | 0.002% | 0.00% | 3.24E-01 | U |
| Epulopiscium | 0.13% | 0.00% | 3.19E-01 | U |
| Filifactor | 0.002% | 0.00% | 1.77E-01 | U |
| Lysinibacillus | 0.001% | 0.00% | 3.24E-01 | U |
| Morganella | 0.001% | 0.00% | 1.61E-01 | U |
| Neisseria | 0.005% | 0.00% | 2.14E-01 | U |
| Novosphingobium | 0.003% | 0.00% | 3.24E-01 | U |
| Paraeggerthella | 0.002% | 0.00% | 3.24E-01 | U |

FIG. 15C

| | | | | |
|---|---|---|---|---|
| Planomicrobium | 0.005% | 0.00% | 1.81E-01 | U |
| Plantibacter | 0.001% | 0.00% | 3.24E-01 | U |
| Proteus | 0.005% | 0.00% | 1.77E-01 | U |
| Providencia | 0.002% | 0.00% | 3.24E-01 | U |
| Pseudomonas | 0.02% | 0.00% | 1.06E-01 | mixed |
| Raoultella | 0.19% | 0.00% | 1.47E-01 | U |
| Stenotrophomonas | 0.42% | 0.00% | 3.24E-01 | U |
| Treponema | 0.002% | 0.00% | 1.98E-01 | U |
| Variovorax | 0.001% | 0.00% | 3.24E-01 | U |
| Pseudoramibacter | 0.001% | 0.00% | 3.24E-01 | A,B |
| Bifidobacterium | 0.001% | 0.00% | 3.24E-01 | L |
| Corynebacterium | 0.002% | 0.00% | 1.74E-01 | L |
| Pediococcus | 0.008% | 0.00% | 3.24E-01 | L |
| Paludibacter | 0.001% | 0.00% | 3.24E-01 | P |
| Bacillus | 0.001% | 0.00% | 3.24E-01 | mixed |

FIG. 21A
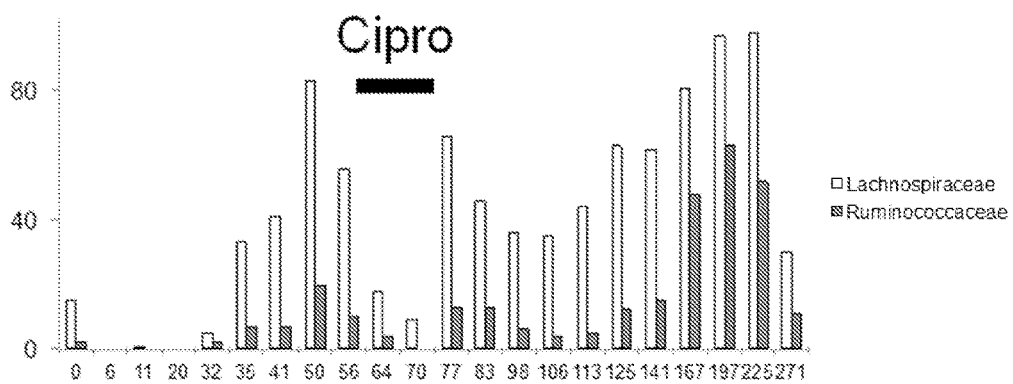
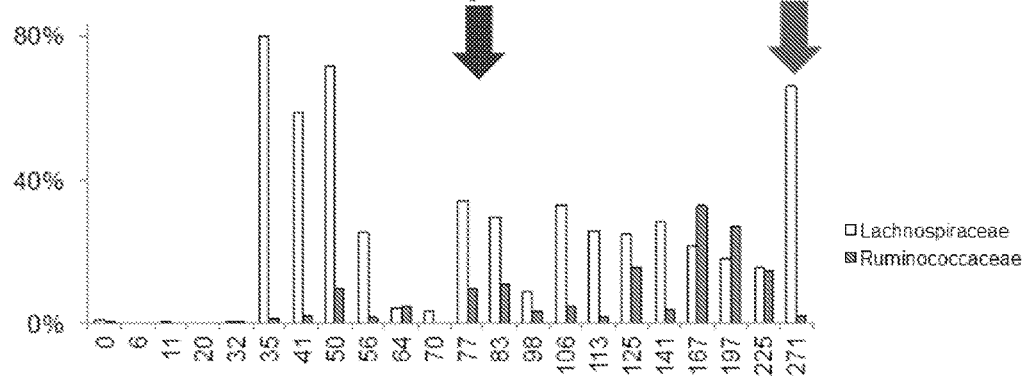
FIG. 21B

BUTYROGENIC BACTERIA AS PROBIOTICS TO TREAT CLOSTRIDIUM DIFFICILE

CROSS-REFERENCE TO RELATED APPLICATIONS

This application is a National Stage Application of International Application No. PCT/US2014/022207,filed Mar. 9, 2014; which claims the benefit of U.S. provisional application Ser. No. 61/793,704, filed Mar. 15, 2013, all of which are incorporated herein by reference in their entirety.

GOVERNMENT SUPPORT

This invention was made with government support under a grant awarded from the National Institutes of Health (NIH) and National Center for Research Resources (NCRR) CTSI Grant 1UL1RR029890. The government has certain rights in the invention.

The Sequence Listing for this application is labeled "SeqList-06Mar14-ST25.txt", which was created on Mar. 6, 2014, and is 2 KB. The entire content is incorporated herein by reference in its entirety.

BACKGROUND OF INVENTION

Some 100 trillion microorganisms inhabit and colonize the human gut (Berg, R. D. "The indigenous gastrointestinal microflora." *Trends Microbiol* 4:430-5. 14 (1996); Young, V. B., and Schmidt, T. M. "Overview of the gastrointestinal microbiota." *Adv. Exp. Med. Biol.* 635:29-40 (2008)). These commensal organisms serve a wide range of functions increasingly recognized as mutualistic and indispensable for the health of the host, including proper digestion, metabolism, and importantly, colonization resistance against pathogens (Guarner, F. "Enteric flora in health and disease." *Digestion* 73 Suppl 1:5-12 (2006)). Alterations of gut microbiota have been linked to asthma, immune system development (Cebra, J. J. "Influences of microbiota on intestinal immune system development." *Am. J. Clin. Nutr.* 69:1046S-1051S (1999)), and inflammatory bowel disease (Frank, D. N. et al., "Molecular-phylogenetic characterization of microbial community imbalances in human inflammatory bowel diseases." *Proc. Natl. Acad. Sci. U.S.A.* 104:13780-13785 (2007)).

*Clostridium difficile* is a major cause of diarrhea in healthcare settings, accounting for 10-20% of antibiotic-associated diarrhea and most cases of colitis associated with antibiotic use. The mortality for *Clostridium difficile* infection is estimated at 1-2.5%, contributing to 15,000-30,000 deaths annually in the U.S. (Ananthakrishnan, A. N. "*Clostridium difficile* infection: epidemiology, risk factors and management," *Nat Rev Gastroenterol Hapatol,* 8:17-26 (2011); Parkes, G. C. et al., "The mechanisms and efficacy of probiotics in the prevention of *Clostridium difficile*-associated diarrhea," *Lancet Infect Dis,* 9:237-44 (2009); and O'Keefe, S. J., "Tube feeding, the microbiota, and *Clostridium difficile* infection," *World J Gastroenterol,* 16:139-42 (2010)). Antibiotic-induced perturbation of gut microbiota is widely believed to provide *C. difficile* an undesirable advantage, allowing it to proliferate and elaborate its toxins in the background of a susceptible flora (see FIG. 16).

*C. difficile* is under the control of the indigenous gut flora, which suppresses the population size of *C. difficile* by a factor of nearly 1 billion fold (Wilson, K. H. "The microecology of *Clostridium difficile.*" *Clin. Infect. Dis.* 16 Suppl 4:S214-8 (1993); Borriello, S. P., and Barclay, F. E. "An in-vitro model of colonisation resistance to *Clostridium difficile* infection." *J. Med. Microbiol.* 21:299-309 (1986)). Randomly selected bacterial isolates from the gut flora are partially effective in suppressing *C. difficile*—a few species, including Lactobacilli, Enterococci, some Bifidobacteria and *Bacteroides* species, have shown varying degrees of inhibitory activity against *C. difficile* (Borriello, S. P., and Barclay, F. E. 1986. Ibid.; Naaber, P. et al. "Inhibition of *Clostridium difficile* strains by intestinal *Lactobacillus* species." *J Med Microbiol* 53:551-4 (2004); Rolfe, R. D. et al. "Bacterial interference between *Clostridium difficile* and normal fecal flora." *J. Infect. Dis.* 143:470-475 (1981); Lee, Y. J. et al. "Identification and screening for antimicrobial activity against *Clostridium difficile* of *Bifidobacterium* and *Lactobacillus* species isolated from healthy infant faeces." *Int J Antimicrob Agents* 21:340-6 (2003)). However, despite the importance of gut flora in *C. difficile* pathogenesis, it remains unclear which components of the gut flora are essential for colonization resistance.

For *C. difficile* to establish infection in the human host, it is generally believed that disruption of gut flora is required. Indeed, antibiotic exposure is the number one risk factor for *C. difficile* infection. The mechanisms by which antibiotic exposure leads to *C. difficile* infection are not clear. Almost all antimicrobials have been implicated. Moreover, the basic ecological features of gut flora that is susceptible to *C. difficile* infection have not been well defined.

Although metronidazole or oral vancomycin is highly effective in suppressing *C. difficile*, it does not prevent relapse. Indeed, 15 to 30 percent of patients relapse within 3 months following antibiotic therapy (Petrella, L. A. et al. "Decreased Cure and Increased Recurrence Rates for *Clostridium difficile* Infection Caused by the Epidemic *C. difficile* BI Strain." *Clin. Infect. Dis* (2012); Pepin, J. et al. "Increasing risk of relapse after treatment of *Clostridium difficile* colitis in Quebec, Canada." *Clin. Infect. Dis.* 40:1591-1597 (2005)). Failure to respond to multiple courses of antimicrobial therapy is not uncommon.

Fecal microbiota transplant (FMT) cures >90% of patients suffering from recurrent *C. difficile* infection (Bakken, J. S. "Fecal bacteriotherapy for recurrent *Clostridium difficile* infection." *Anaerobe* 15:285-9 (2009); Borody, T. J. "'Flora Power'—fecal bacteria cure chronic *C. difficile* diarrhea." *Am J Gastroenterol* 95:3028-9 (2000); Famularo, G. et al., "Fecal bacteriotherapy or probiotics for the treatment of intestinal diseases?" *Am J Gastroenterol* 96:2262-4 (2001); Brandt, L. J. et al., "Long-Term Follow-Up of Colonoscopic Fecal Microbiota Transplant for Recurrent *Clostridium difficile* Infection." *Am. J. Gastroenterol.* (2012); Russell, G. et al., "Fecal bacteriotherapy for relapsing *Clostridium difficile* infection in a child: a proposed treatment protocol." *Pediatrics* 126:e239-42.), but FMT has not gained widespread popularity due to the lack of aesthetic appeal and concern of potential infection risks.

BRIEF SUMMARY

The subject invention provides nonpathogenic, butyrogenic bacterial strains for use in treating and/or preventing *C. difficile* infection (CDI). In particular, the invention pertains to the use of such bacterial strains in modulating the microbial flora in a mammal.

In a first aspect, the present invention provides a nutritional or pharmaceutical composition comprising a nonpathogenic butyrogenic bacterial strain or comprising a mixture of bacterial strains, including at least one butyrogenic bacterial strain, to prevent and/or treat CDI.

Thus, in one aspect, the invention relates to the use of butyrogenic bacterial strains, for preparing a composition for the following applications: (1) preventing and/or treating CDI, and/or (2) modulating the balance of the microbial flora in the gut by advantageously promoting the antimicrobial activity of the bacterial flora against *C. difficile*.

In one embodiment, a strain of bacteria of the Ruminococcaceae or Lachnospiraceae family is used. In a specific embodiment, the subject invention uses one or more of the following butyrogenic bacteria: *Blautia, Pseudobutyrivibrio, Roseburia, Faecalibacterium, Anaerostipes, Subdoligranulum, Ruminococcus, Streptococcus, Dorea,* and *Coprococcus*.

In a third aspect, the present invention provides a method for preventing and/or treating CDI that comprises the step of administering to a mammal an affective amount of a composition comprising a selected bacterial strain or a mixture of selected bacterial strains. The method may include the step of diagnosing CDI in the mammal. The method may also include the step of monitoring the CDI in the mammal.

This prevention and/or treatment method may be performed under the direction of a physician or a health professional. In this case, the health professional decides upon the dose, the duration of treatment and also a possible combination of the selected nonpathogenic, butyrogenic bacterial strains with other active principles effective in preventing and/or treating CDI. Alternatively, therapeutic and/or prophylactic use of a composition of the invention can be performed by the user.

The present invention further provides methods for preventing and/or treating CDI. This prevention and/or treatment may be carried out via regulation of the gases produced in the colon, through modulating the microbial flora.

BRIEF DESCRIPTION OF THE SEQUENCES

SEQ ID NO:1 is an artificial oligonucleotide sequence for a reverse primer (534R).

SEQ ID NO:2 is an artificial oligonucleotide sequence for the corresponding forward primer.

SEQ ID NO:3 is an artificial oligonucleotide sequence for a forward primer to detect *C. difficile*.

SEQ ID NO:4 is an artificial oligonucleotide sequence for a reverse primer to detect *C. difficile*.

BRIEF DESCRIPTION OF THE DRAWINGS

FIG. 1A is a Shannon diversity index that was used to estimate microbial diversity in each group. FIG. 1B is a species evenness index that was calculated using the formula J'=H'/H'max, where H' is the Shannon diversity index and H'max is the maximum value of H' (=ln S, where S is total number of species in the community). FIG. 1C is a species richness index that is defined as the number of refOTUs identified in each sample. All three indices were significantly lower in the CDI and the CDN group compared to healthy controls (Student's t-test). No significant difference was observed between the CDI and the CDN group.

FIG. 2A is a scatterplot that illustrates the microbial communities between *C. difficile*-positive fecal samples (CDI), *C. difficile*-negative diarrheal samples (CDN), and healthy controls (HC). Unweighted UniFrac was used to generate the distances between *C. difficile*-positive fecal samples, *C. difficile*-negative diarrheal samples, and healthy controls. Scatterplots were then generated using Principal Coordinate Analysis (PCoA). The percentage of variation explained by each PCoA is indicated on the axes. Each point represents a microbial community. The difference among communities between CDI and HC was significant with $p<0.001$ (t-test with permutation). FIGS. 2B and 2C are graphical illustrations of the average Unifrac distance between pairs of samples within each group, indicating a greater heterogeneity in gut microbial communities in both the CDI and CDN groups compared to healthy controls. Error bars are shown as the standard error of the mean.

FIG. 3A shows the mean proportion of Firmicutes sequences was lower in the CDI and CDN group ($p=5.70\times10^{-7}$ and $1.08\times10^{-8}$, respectively; Student's t-test) compared to the healthy controls (HC). FIG. 3B shows the comparison of the number of bacterial phylotypes (refOTUs) in the major phyla among the three groups. The mean number of Firmicutes phylotypes was lower in the CDI and CDN groups ($p=8.81\times10^{-19}$ and $p=7.16\times10^{-16}$; Student's t-test) compared to HC.

FIG. 4A shows the proportion of bacterial taxa in each sample inferred from 16S rDNA sequence data. Each column corresponds to an individual fecal sample. Each row corresponds to a specific bacterial phylotype or refOTUs, arrayed based on phylogenetic relationship. Only the most prominent refOTUs (>0.1% abundance) are included in this heatmap. The relative abundance of each phylotype is represented by the key code. FIG. 4B shows the proportion of bacterial taxa within *Clostridium* clusters. Each column represents an individual fecal sample. Each row corresponds to a refOTU assigned to one of the 19 *Clostridium* clusters. Members of the *Clostridium* clusters XIVa and IV are shaded.

FIG. 5A shows the top 10 genera most differentially depleted in *C. difficile*-associated microbiota versus healthy controls that were identified by Linear discriminant analysis (LDA) coupled with effect size measurements, most of which are butyric-acid producing anaerobic bacteria. Bacterial taxa depleted in CDI are indicated with a positive LDA score, and taxa enriched in CDI are indicated with a negative score. Only the taxa that meet an LDA significant threshold of 3.6 are shown. FIG. 5B shows the inter-individual variation in the relative abundance of selected genera. The overall abundance (sequence reads, y-axis) of the 10 most differentially depleted genera in CDI (indicated in the key at right) is significantly lower in CDI compared to the healthy controls ($p=4.0\times10^{-21}$, Student's t-test). Each bar corresponds to an individual sample.

FIGS. 6A-6D show the relative proportions of acetate, butyrate, and lactate fermenters in gut microbiota. FIG. 6A shows the sequence reads that were classified at the genus level according to the primary metabolic end product of carbohydrate fermentation and compared using Student's t-test. A=acetate, B=butyrate, L=lactate. Genera that were ambiguously defined as producing both acetate and butyrate, or other short chain fatty acids (SCFA) such as succinate, propionate, formate, or ethanol were excluded in this analysis—most of which are minor constituents of the gut microbiota (<1% of sequence reads). Error bars are shown as the standard error of the mean. FIG. 6B shows the relative proportions of major butyrate-producing bacteria, FIG. 6C shows the relative proportions of major acetogens by genera, and FIG. 6D shows the relative proportions of primary lactic-acid producing organisms.

FIG. 8A is a Shannon diversity index. FIG. 8B is a species evenness index. FIG. 8C is a species richness index. Subjects were classified as mild (n=18), moderate (n=11), and severe to severe-complicated (n=5) according to the SHEA/IDSA practice guideline on the clinical definition of CDI disease severity (Cohen, S. H. et al., Society for Healthcare Epidemiology of America, and Infectious Diseases Society of America. 2010. Clinical practice guidelines for *Clostridium difficile* infection in adults: 2010 update by the society for healthcare epidemiology of America (SHEA) and the infectious diseases society of America (IDSA). *Infect. Control Hosp. Epidemiol.* 31:431-455).

FIG. 9A is a Shannon diversity index. FIG. 9B is a species evenness index. FIG. 9C is a species richness index. Subjects were classified according to recurrent disease (n=9) versus first time diagnosis (n=29). Recurrent disease was defined as subjects who had a prior history of diarrhea with *C. difficile* positive stools.

FIG. 11A: HC; FIG. 11B: CDI; and FIG. 11C: CDN.

FIG. 12A: *Bacteroides*; FIG. 12B: *Fusobacterium*; FIG. 12C: *Lactobacillus*, and FIG. 12D: *Streptococcus*. Subjects with CDI and healthy controls are ordered from left to right according to increasing proportions of reads that were assigned to the genera indicated. A high proportion of sequence reads was observed in some subjects.

FIG. 14 is a table providing DNA barcode used for each stool sample, the number of reads per sample, and the proportion of reads retained after quality control.

FIG. 15 is a table providing the major genera classified according to the dominant fermentation end-product(s). For each genus, the proportions of pyrosequence reads for CDI and Healthy Controls (HC) are shown with p-values (Student's t-test). Abbreviations: A=acetate, B=butyrate, E=ethanol, F=fumarate, M=mixed (assorted C2-C4 compounds), L=lactate, Propionate, S=succinate, U=uncharacterized). Uncultured, unknown phylotypes, and taxonomy of uncertain placement (Incertae sedis) were not included in this analysis.

" FIG. 18A is an illustration of the number of operational taxonomic units (OTU) of a group of species over time and FIG. 18B is an illustration of the proportion of OTUs over time.

" FIG. 19A is an illustration of the number of operational taxonomic units (OTU) of a group of species over time and FIG. 19B is an illustration of the proportion of OTUs over time.

FIG. 20A is an illustration of the number of operational taxonomic units (OTU) of a group of species over time and FIG. 20B is an illustration of the proportion of OTUs over time.

FIGS. 21A and 21B are graphical illustrations of the incomplete recovery of Lachnospiraceae and Ruminococcaceae sequences prior to *C. difficile* relapse. FIG. 21A is an illustration of the number of operational taxonomic units (OTU) of a group of species over time and FIG. 21B is an illustration of the proportion of OTUs over time.

DETAILED DISCLOSURE

Figure 1A:
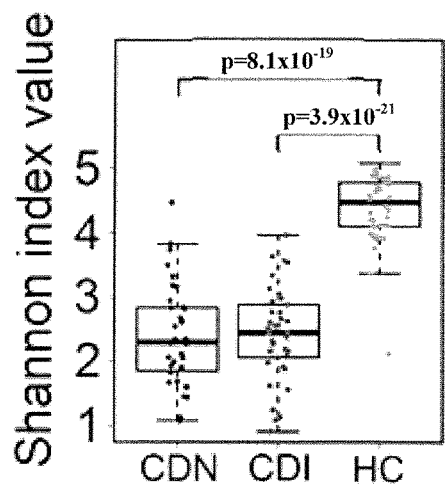
FIGS. 1A-1C show the decreased microbial diversity, evenness, and species richness in gut microbiota associated with *C. difficile* infection.

The present invention provides materials and methods for treating and/or preventing a CDI.

In one embodiment, the subject invention provides a composition comprising at least one nonpathogenic, butyrogenic bacterial strain or a mixture of bacterial strains that include at least one butyrogenic bacterial strain. In another embodiment of the invention, a method for treating and/or preventing CDI is provided that comprises the step of administering to a mammal an effective amount of a composition comprising at least one nonpathogenic, butyrogenic bacterial strain or a mixture of bacterial strains that include at least one butyrogenic bacterial strain in treating and/or preventing the CDI.

In one embodiment, a strain of bacteria of the Ruminococcaceae or Lachnospiraceae family is used. In a specific embodiment, the subject invention uses one or more of the following butyrogenic bacteria: *Blautia, Pseudobutyrivibrio, Roseburia, Faecalibacterium, Anaerostipes, Subdoligranulum, Ruminococcus, Streptococcus, Dorea,* and *Coprococcus.*

According to the subject invention, 549,643 partial prokaryotic 16S rRNA gene sequences from *C. difficile*-positive, *C. difficile*-negative diarrheal samples and samples from healthy controls were examined, from which 3,531 bacterial phylotypes from 115 fecal specimens were identified. Microbiome analysis revealed significant alterations in microbial community structure associated with CDI, which was accompanied by markedly decreased microbial diversity and fewer bacterial phylotypes compared to healthy controls. Several essential butyrate and short-chain fatty acid (SCFA) producing bacteria were identified as being either absent or markedly depleted in CDI, all of which are members of the *Clostridium* clusters IV and XIVa. These results suggest a conserved set of core organisms in the human gut that are important against *C. difficile* infection. Based on these results, candidate organisms were identified for use in the subject probiotics-based therapeutic approaches for CDI.

The term "mammal" according to the present invention refers to both monogastric mammals and polygastric mammals. Humans, felines and canines are particularly intended, especially domesticated mammals.

The term "nonpathogenic" is intended to mean a microbial species for which no pathology of the host associated with its presence has been demonstrated (strain GRAS=Generally Recognized As Safe).

A composition of the invention can be, for example, a nutritional composition or a pharmaceutical composition. A nutritional composition of the invention is one that may be enterally consumed in any form, such as a food product. A pharmaceutical composition of the invention comprises at least one bacterial strain of the invention that is useful in treating and/or preventing CDI. A pharmaceutical composition comprises at least one bacterial strain of the invention that is combined with a pharmaceutically acceptable carrier, which may comprise excipients. It is preferably administered orally or directly in situ, e.g., rectally via suppositories.

The composition according to the invention may be administered orally, in the form of capsules, tablets, powders, granules, solutions, or suspensions. The at least one bacterial strain can be mixed with conventional excipients, such as gelatin, starch, lactose, magnesium stearate, talc, gum arabic and the like. It may also be advantageous to use less conventional excipients that, for example, make it possible to increase the ability of the at least one bacterial strain used to be active in the gut. For example, cellobiose, maltose, mannose, salicine, trehalose, amygdalin, arabinose, melobiose, rhamnose and/or xylose may be added. This list is not exhaustive and the substrates are chosen and adapted as a function of the strain considered. These substrates may promote growth of the at least one butyrogenic strain present in the composition.

Thus, the composition preferably comprises at least one additive which promotes the activity of the at least one strain in the digestive environment.

In a particular embodiment of the invention, the at least one nonpathogenic, butyrogenic bacterial strain present in the pharmaceutical and/or nutritional composition is administered in a form which allows it to be active in the gut (e.g., colon). In particular, it is necessary for the bacterial strain to be alive, or viable, in the digestive tract. After production of the bacterial strain and, depending on the methods of production, it is also possible to maintain this strain under anaerobic packaging conditions in order to enable it to remain viable.

In a preferred embodiment, the at least one nonpathogenic, butyrogenic bacterial strain is packaged in an anaerobic environment, i.e., it is packaged in an oxygen-free atmosphere.

According to the subject invention, a method is provided for preventing and/or treating CDI that comprises the step of administering to a mammal an affective amount of a composition comprising a selected bacterial strain or a mixture of selected bacterial strains. The method may include the step of: diagnosing the CDI in the mammal and/or monitoring the CDI in the mammal. Thus, according to one embodiment of the invention, the CDI bacterial strain can be isolated from the digestive system, in particular from the feces, of the mammal.

In a particular embodiment, a method for specifically monitoring and/or diagnosing the *C. difficile* bacterial strain in the digestive tract of a mammal comprises the following steps: defining a nucleotide sequence (probe or primer) specific for the *C. difficile* strain; detecting and/or quantifying said strain by hybridization of the probe with nucleic acid extracted from the fecal flora, or with the fecal bacteria attached to a slide. For example, detection of nucleic acids (DNA or RNA) of *C. difficile* can be performed by PCR or RT-PCR or by hybridization with specific probes (Southern or Northern).

In order to carry out such a diagnosing and/or monitoring step, diagnostic kits, which are also objects of the present invention, can be used. Such kits can contain a "standard" in order to be able to evaluate the amount of bacterial strain(s) in the feces.

Preparation of Bacterial Strain

Bacterial strains useful according to the subject invention may be obtained commercially and/or produced by a fermentation process and, optionally, drying.

According to one embodiment, a method for producing a butyrogenic bacterial strain, for its use as defined above, comprises the following steps: the strain is grown on a suitable medium, under conditions of strict anaerobiosis, in the presence of a carbon-based substrate and/or of $H_2/CO_2$ as energy source; the bacterial cells are recovered; the bacterial cells are packaged.

A preferred method for recovering the bacterial cells is centrifugation, for example between 10,000 g and 15,000 g, advantageously 12,000 g, for 15 to 20 minutes.

The bacteria may be washed in, for example, an anaerobic phosphate buffer, by resuspension of the cells, agitation, and a further centrifugation step.

Preparation of Compositions of the Invention

The selected bacterial strain(s) may be in a dried form. The drying of bacterial strains after production by fermentation is known to the skilled person. See for example, EP 0 818 529 (SOCIETE DES PRODUITS NESTLE), which is incorporated by reference in its entirety, where a drying process of pulverisation is described, or WO 0144440 (INRA), which is also incorporated by reference in its entirety. Usually, bacterial microorganisms are concentrated from a medium and dried by spray drying, fluidised bed drying, lyophilisation (freeze drying) or other drying process. Micro-organisms can be mixed, for example, with a carrier material such as a carbohydrate such as sucrose, lactose or maltodextrin, a lipid or a protein, for example milk powder during or before the drying.

The bacterial strain need not necessarily be present in a dried form. It may also be suitable to mix the bacteria directly after fermentation with a food product and, optionally, perform a drying process thereafter. Such an approach is disclosed in PCT/EP02/01504) (SOCIETE DES PRODUITS NESTLE), which is incorporated by reference in its entirety. Likewise, a probiotic composition of the subject invention may also be consumed directly after fermentation. Further processing, for example, for the sake of the manufacture of convenient food products, is not a precondition for the beneficial properties of the bacterial strains provided in the probiotic composition.

The compositions according to the present invention may be enterally consumed in any form. They may be added to a nutritional composition, such as a food product. On the other hand, they may also be consumed directly, for example in a dried form or directly after production of the biomass by fermentation.

According to the subject invention, the bacterial strain(s) can be provided in an encapsulated form in order to ensure a high survival rate of the micro-organisms during passage through the gastrointestinal tract or during storage or shelf life of the product.

The compositions of the subject invention may, for example, be provided as a probiotic composition that is consumed in the form of a fermented, dairy product, such as a chilled dairy product, a yogurt, or a fresh cheese. In these later cases, the bacterial strain(s) may be used directly also to produce the fermented product itself and has therefore at least a double function: the probiotic functions within the context of the present invention and the function of fermenting a substrate such as milk to produce a yogurt.

If the bacterial strain is added to a nutritional formula, the skilled person is aware of the possibilities to achieve this. Dried, for example, spray dried bacteria, such as obtainable by the process disclosed in EP 0 818 529 (which is incorporated herein by reference in its entirety) may be added directly to a nutritional formula in powdered form or to any other food product. For example, a powdered preparation of the bacterial strain(s) of the invention may be added to a nutritional formula, breakfast cereals, salads, a slice of bread prior to consumption.

Bacterial strain(s) of the invention may be added to a liquid product, for example, a beverage or a drink. If it is intended to consume the bacteria in an actively-growing state, the liquid product comprising the bacterial strain(s) should be consumed relatively quickly upon addition of the bacteria. However, if the bacteria are added to a shelf-stable product, quick consumption may not be necessary, so long as the bacterial strain(s) are stable in the beverage or the drink.

WO 98/10666, which is incorporated herein by reference in its entirety, discloses a process of drying a food composition and a culture of probiotic bacteria conjointly. Accordingly, the subject bacterial strain(s) may be dried at the same time with juices, milk-based products or vegetable milks, for example, yielding a dried product already comprising probiotics. This product may later be reconstituted with an aqueous liquid.

Quantity of Probiotics

Although it is not mandatory, probiotic bacteria may be consumed in the living state with the intention that the probiotic micro-organisms arrive intactly in the small and large intestines the latter of which may be colonized. If this is the case, a sufficient dose of bacteria is usually consumed per day in order to achieve successful colonization. The skilled person is aware of these daily doses, which depend on the micro-organisms but generally are in the range of $10^6$ to $10^{14}$, preferably $10^7$ to $10^{13}$ cfu per day.

However, the teaching of the present invention may also be achieved with dead probiotics, with the fermented media or simply with the substrate for the probiotics, which usually is prebiotic fiber.

Hence, the fermented media, even if essentially free of probiotics but comprising metabolites of probiotics, may be used to work the present invention.

In other words, dead or living probiotics, their medium, substrate or metabolites may be directly added to food products in the same or a similar way as set forth above for living probiotics more specifically. The fermented medium, substrate or metabolites may be separated from the bacteria after fermentation by centrifugation or filtration, for example. The supernatant or the filtrate may then be concentrated, chilled, frozen, dried, for example, spray dried or directly used for enteral administration to an individual. If fermented medium is dried, it may be powdered and, as described above for the living bacterial strain(s), added to any food product.

If supernatant or fermentation medium is to be administered to a human, the effective amount is in the range of 0.5 to 3 dl, preferably 1 to 2 dl of growth medium, harvested after 30 to 50 hrs, preferably 45 to 50 hrs of bacterial growth. When density of bacteria is estimated at an OD600 nm, an OD of 2 to 7 is routinely obtained, which represents the respective growth of 2 to $7 \times 10^8$ bacteria per ml. The supernatant may be administered after removal of the bacteria by filtration, for example.

Example 1

Methods

Subjects and Sample Collection

The University of Florida Institutional Review Board reviewed the study design. Stool samples positive (CDI) and negative (CDN) for *C. difficile*, defined based on results of ELISA (C. Diff Quik Chek Complete™, Techlab, Blacksburg, Va.) or GeneXpert multiplex PCR for detection of toxin B gene (Cepheid, Sunnyvale, Calif.), were obtained from the Clinical Microbiology Laboratory at Shands Hospital at the University of Florida. Fecal samples from healthy individuals were collected from subjects undergoing screening colonoscopy and were analyzed in parallel as controls. Toxin B (tcdB gene) specific PCR (Kuhl, S. J., Tang, Y. J., Navarro, L., Gumerlock, P. H., and J., S., Jr. 1993. Diagnosis and monitoring of *Clostridium difficile* infections with the polymerase chain reaction. *Clin Infect Dis* 16 Suppl 4:S234-8; Gumerlock, P. H., Tang, Y. J., Meyers, F. J., and Silva, J., Jr. 1991. Use of the polymerase chain reaction for the specific and direct detection of *Clostridium difficile* in human feces. *Rev. Infect. Dis.* 13:1053-1060; Kato, N., Ou, C. Y., Kato, H., Bartley, S. L., Luo, C. C., Killgore, G. E., and Ueno, K. 1993. Detection of toxigenic *Clostridium difficile* in stool specimens by the polymerase chain reaction. *J Infect Dis* 167:455-8; and Alonso, R., Munoz, C., Gros, S., Garcia de Viedma, D., Pelaez, T., and Bouza, E. 1999. Rapid detection of toxigenic *Clostridium difficile* from stool samples by a nested PCR of toxin B gene. *J. Hosp. Infect.* 41:145-149.) was performed in all 115 samples (Example 2; Methods).

DNA Extraction, Bacterial 16S rDNA Gene Amplification, and Sequence Analysis

Figure 7:
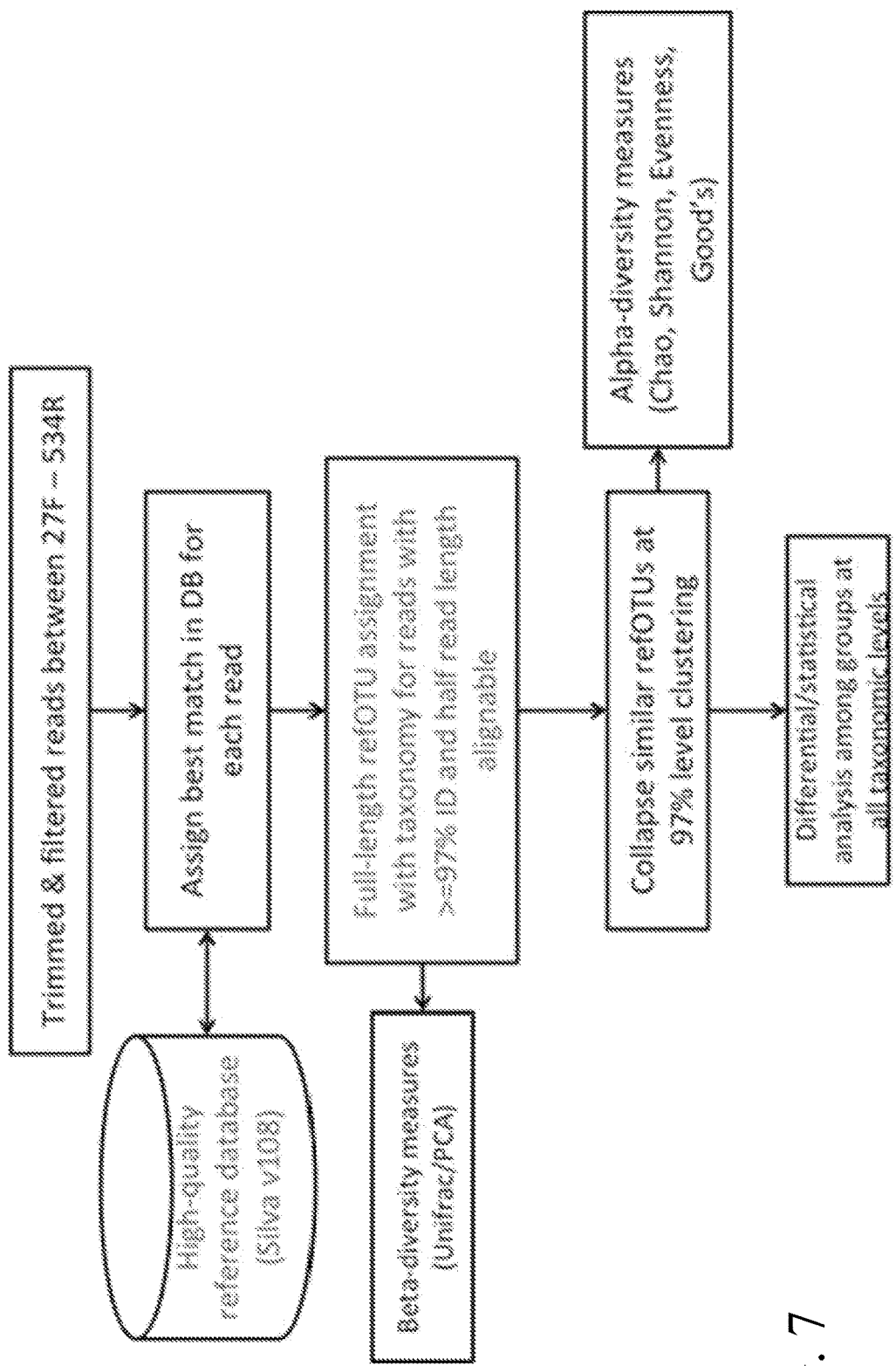
FIG. 7 is an illustration of a computational pipeline for classification of 454 sequence reads.

Genomic DNA was extracted from each fecal specimen using a bead-beating, solvent extraction method (MO-BIO PowerSoil DNA Isolation Kit, Mo Bio, Carlsbad, Calif.). The V1-V3 hypervariable region of bacterial 16S rRNA gene segments was amplified in 4 replicates using broad-range rRNA PCR primers 27F and 534R and the PCR products pooled. The reverse primer (534R) included a barcode sequence unique to each sample, allowing PCR amplicons to be multiplexed and sequenced simultaneously. The amplicons were gel purified, pooled, and subjected to pyrosequencing using the Titanium chemistry on the Roche/454 GS-FLX platform. Pyrosequence reads were filtered, trimmed, and aligned to the SILVA non-redundant 16S reference database, release 108 (Pruesse, E., Quast, C., Knittel, K., Fuchs, B. M., Ludwig, W., Peplies, J., and Glockner, F. O. 2007. SILVA: a comprehensive online resource for quality checked and aligned ribosomal RNA sequence data compatible with ARB. *Nucleic Acids Res* 35:7188-96.). Reads were assigned taxonomic classifications using USEARCH (version 5.1), and de-replicated to unique reference sequence-based operational taxonomic units (refOTU) using UCLUST (version 5.0) (FIG. 7).

Statistical Methods

Weighted and Unweighted Unifrac (Lozupone, C., Lladser, M. E., Knights, D., Stombaugh, J., and Knight, R. UniFrac: an effective distance metric for microbial community comparison. *Isme J.*) was used to measure β diversity between microbial communities and plotted using Principal Coordinate Analysis. Comparisons between phylogenetic taxa were calculated using unpaired t-test (Graphpad, La Jolla, Calif.) and Minitab v.15 at α<0.05. Heat maps were generated using R and Matrix2png (Pavlidis, P., and Noble, W. S. 2003. Matrix2png: a utility for visualizing matrix data. *Bioinformatics* 19:295-296.). LEfSe (Segata, N., Izard, J., Waldron, L., Gevers, D., Miropolsky, L., Garrett, W. S., and Huttenhower, C. 2011. Metagenomic biomarker discovery and explanation. *Genome Biol.* 12:R60.) was used to identify bacteria taxa that are differentially abundant or depleted between sample groups.

Results

Samples and Acquisition of 16S Sequence Data

As discussed above, microbial communities in 39 specimens positive for *C. difficile* (CDI group), 36 *C. difficile*-negative diarrheal samples (CDN group), and 40 stool samples from healthy controls (HC) were sampled (Table 1). Of the 39 samples in the CDI group, 29 were from subjects with initial episodes and 10 samples were from recurrences. Genomic DNA was extracted from each specimen and the V1-V3 hypervariable region of bacterial 16S rRNA gene segments was amplified using broad-range rRNA PCR primers 27F and 534R and the amplicons were pooled and deep sequenced. After trimming and quality control (Table 2; FIG. 7), a total of 526,071 partial V1-V3 high-quality 16S rRNA sequence reads were available for analysis (~4,780 reads per sample with an average amplicon length of ~492 nt). Sequences from all 115 samples were equally represented.

TABLE 1

Subject demographics and samples used in this study

|  | HC | CDI | CDN |
|---|---|---|---|
| Number of samples | 40 | 39 | 36 |
| Median Age | 60 y.o. | 57 y.o. | 61 y.o. |
| % Female | 70% | 41% | 52% |
| Caucasian | 27 | 28 | 24 |
| African-American | 3 | 9 | 9 |
| Nursing Home | 0 | 68% | 72% |

HC: healthy controls,
CDI: *C. difficile* infection,
CDN: subjects with diarrhea but *C. difficile* negative

TABLE 2

Pyrosequencing data analysis. The number of pyrosequence reads obtained and quality control filtering of raw reads.

|  | HC | CDI | CDN | All Subjects |
|---|---|---|---|---|
| Number of subjects | 40 | 39 | 36 | 115 |
| Total number of raw reads | 246,765 | 178,910 | 191,891 | 617,566 |
| Total reads after quality control | 219,093 | 159,045 | 171,505 | 549,643 |
| % reads retained | 88.79% | 88.90% | 89.38% | 89.00% |
| Average post-filtered reads per subject Quality-filtering | 5,477 | 4,078 | 4,764 | 4,780 |
| Total reads(post-filter) matching refOTU | 211,764 | 147,510 | 166,797 | 526,071 |
| % reads matched to refOTU >97% post-filter | 96.65% | 92.74% | 97.25% | 95.71% |
| Average post-filtered, refOTU matched | 5,294 | 3,782 | 4,633 | 4,575 |
| Average amplicon size(excluding primers) | 490 | 492 | 495 | 492 |
| Total number of refOTUs | 2,986 | 1,392 | 1,582 | 3,531 |
| Average refOTUs per subject | 368 | 104 | 122 | 202 |

Figure 1B:
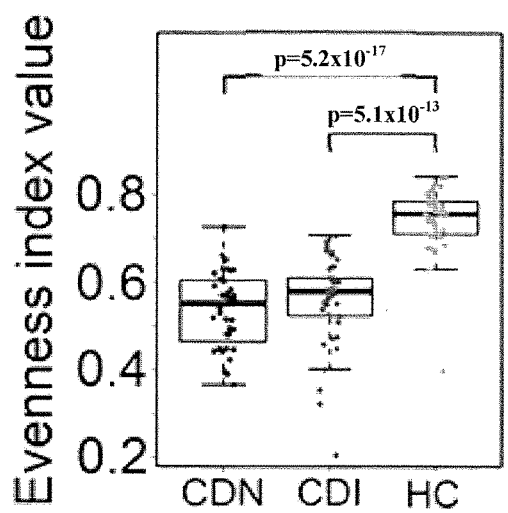
Figure 1C:
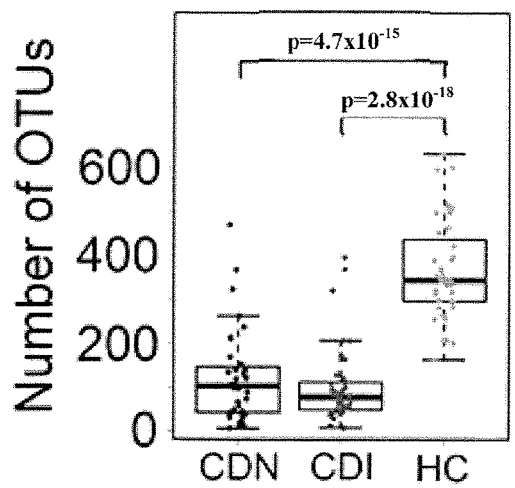
Figure 8A:
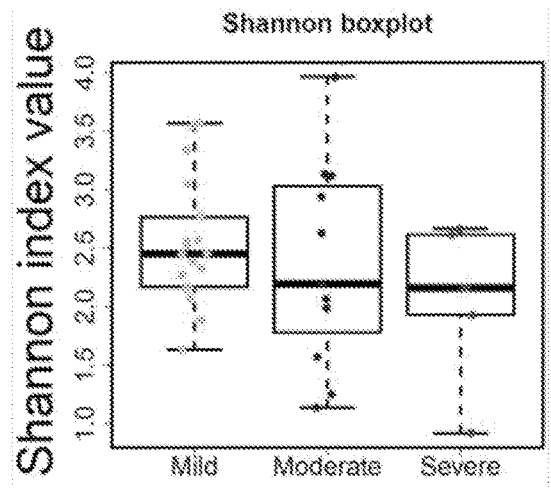
FIGS. 8A-8C show gut microbial diversity, evenness, and species richness that did not differ significantly according to disease severity.
Figure 8B:
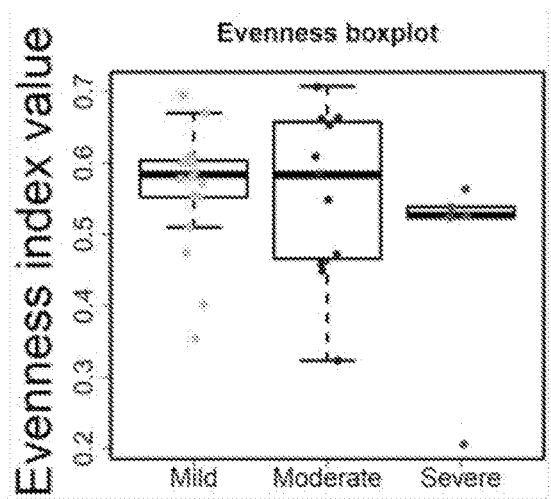
Figure 8C:
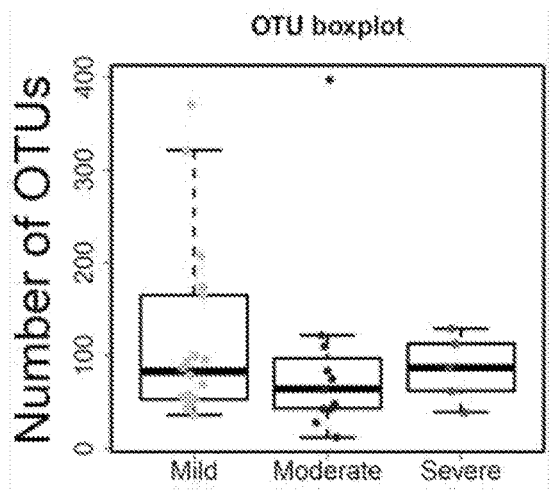
Figure 9A:
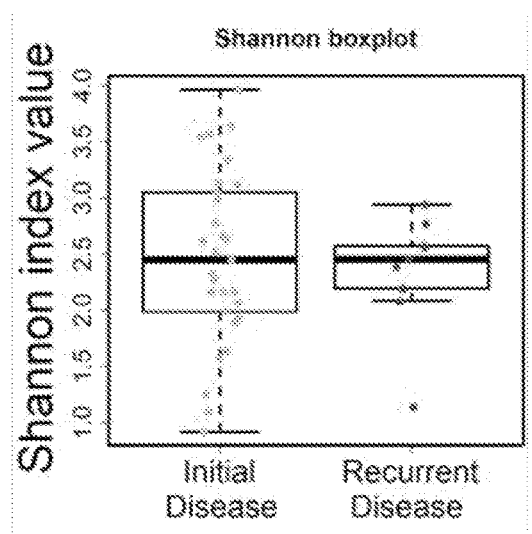
FIG. 9A-9C show gut microbial diversity, evenness, and species richness that did not differ significantly between initial and recurrent disease.
Figure 9B:
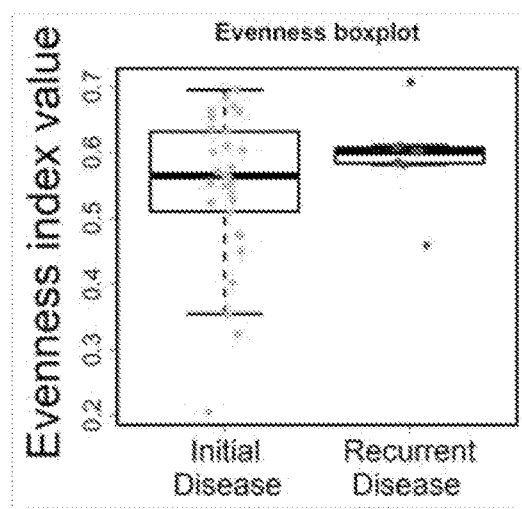
Figure 9C:
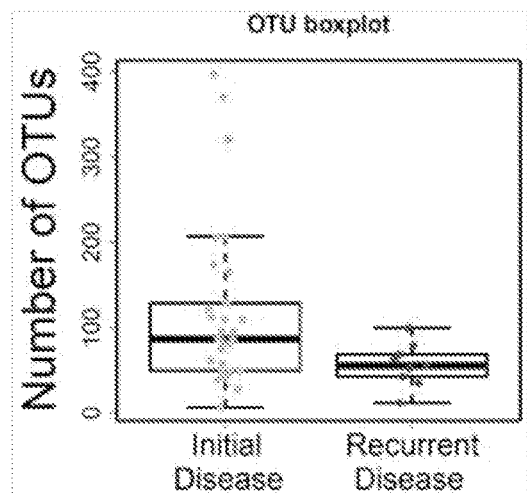

HC: healthy controls,
CDI: *C. difficile* infection,
CDN: subjects with diarrhea but *C. difficile* negative Microbial Diversity and Richness of Gut Microbiota During *C. difficile* Infection A total of 3,531 refOTUs from 115 fecal samples, which belonged to 150 different genera in 15 different phyla, were identified. 2,986 of the 3,531 refOTUs (84.6%) identified were found in healthy controls. In contrast, only 1,392 (39.4%) and 1,582 (44.8%) refOTUs were detected in the CDI and the CDN group, respectively. Among the most abundant refOTUs (defined as >0.1% of all pyrosequencing reads), 124 were shared in more than half of the healthy controls but only 9 were detected in at least one-half of the samples in the CDI group. Species richness was significantly lower in the CDI and the CDN groups compared to healthy controls, and both the microbial diversity (as determined by Shannon diversity index) and species evenness were markedly reduced (FIG. 1). Microbial richness and diversity did not differ between CDI and CDN (p>0.05). For the CDI group, when samples were stratified by disease severity, no difference in microbial diversity or species richness was observed (FIG. 8). Comparison of initial versus recurrent disease revealed a trend toward lower species richness in recurrent disease; however, no significant difference in gut microbial diversity was observed (FIG. 9). Taken together, these data demonstrate that many of the normally abundant phylotypes were depleted during CDI, and suggest that factors other than gut microbiota may modulate disease severity.

Intestinal Dysbiosis in CDI

Figure 2A:
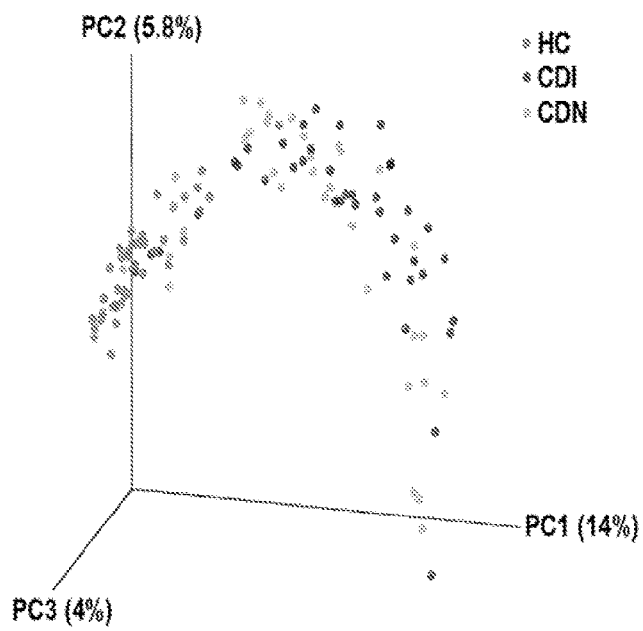
FIGS. 2A-2C show the comparison of microbial communities.
Figure 2B:
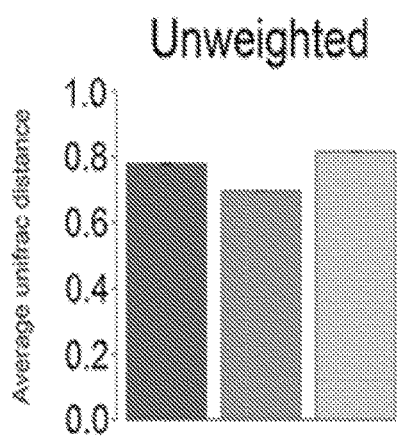
Figure 2C:
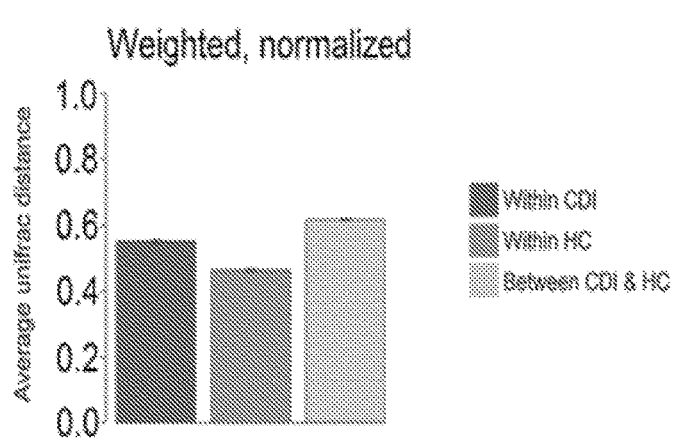

To characterize the global changes in microbial community structure, the UniFrac method (Lozupone, C. et al. "UniFrac: an effective distance metric for microbial community comparison." *Isme J.*) was applied to analyze phylogenetic relatedness of pyrosequence reads from all samples. In both weighted and unweighted UniFrac analysis, gut microbial communities associated with CDI clustered separately from healthy controls (FIG. 2A). Calculation of Unifrac distances within and between groups revealed that microbial communities within the CDI group were more similar to one another than to microbial communities in healthy subjects (FIG. 2B). The average UniFrac distance between pairs of samples within the CDI group was significantly higher than pairs of samples within healthy controls (FIG. 2B), indicating greater heterogeneity in gut microbial communities associated with CDI. No appreciable differences in community structure or membership were observed between the CDI and CDN groups. Thus, the greatest amount of variation among all samples was explained by disease state (i.e. diarrhea versus health), and inter-individual differences accounted for most of the remaining variability in the data. These results support the conclusion that distal gut microbiota associated with CDI are significantly altered and disordered.

Paucity of Firmicutes in the Aggregate Gut Microbiota Associated with CDI

Figures 3A, 3B:
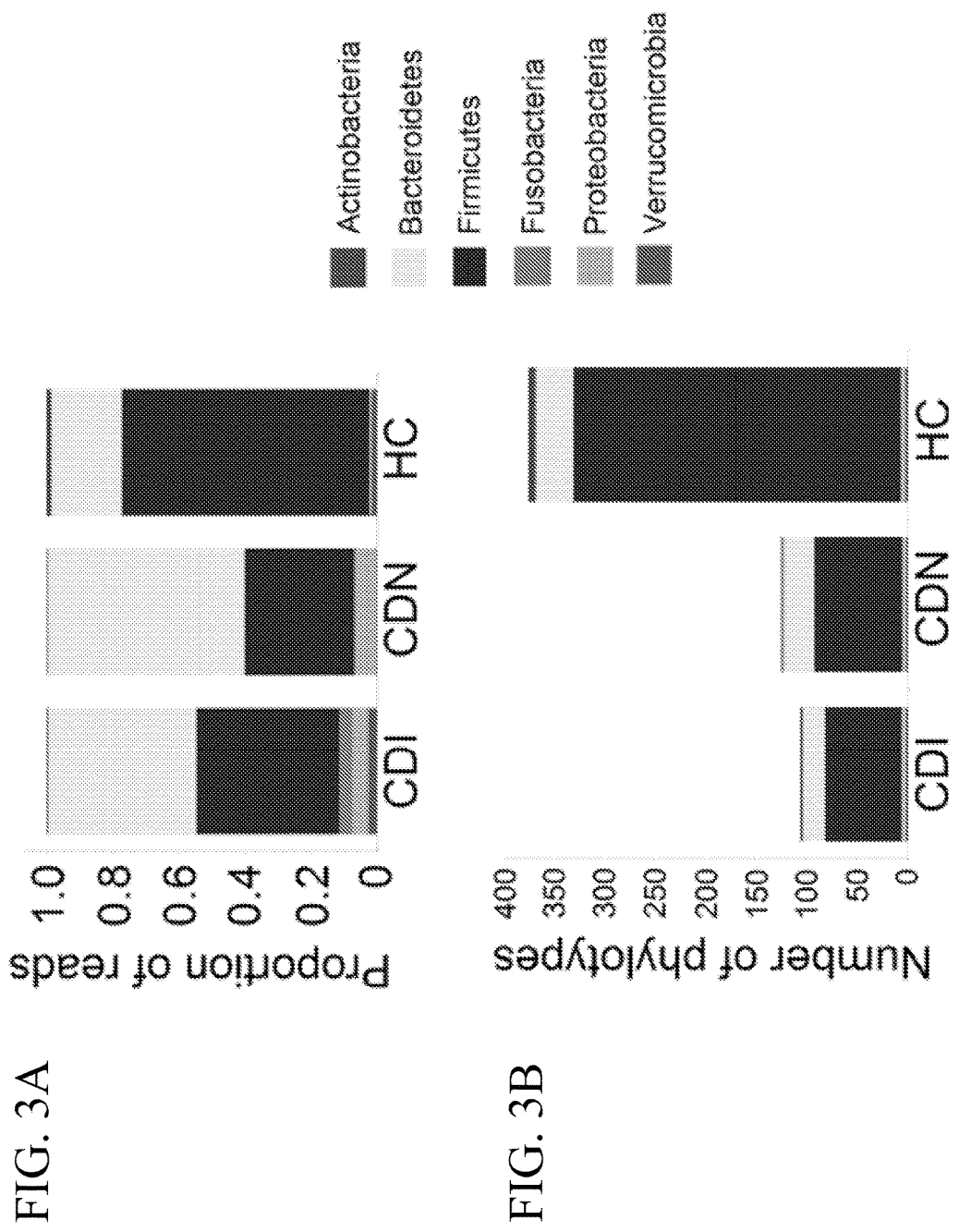
FIGS. 3A-3B show the paucity of Firmicutes sequences and phylotypes in *C. difficile*-associated aggregate gut microbiota.

The Firmicutes phylum harbors the most numerous and diverse bacterial species in the human gut. In healthy controls, Firmicutes sequences were dominant at 74.9% of all reads (averaging ~322 phylotypes per subject; FIG. 3). Only 21.5% of all reads were assigned to the Bacteroidetes phylum, represented by ~37 phylotypes per subject. This feature of Firmicutes-dominant aggregate fecal microbiota in healthy subjects is in concordance with several previous reports for younger individuals (Costello, E. K. et al. "Bacterial community variation in human body habitats across space and time. *Science* 326:1694-7 (2009); Wu, G. D. et al. "Sampling and pyrosequencing methods for characterizing bacterial communities in the human gut using 16S sequence tags. *BMC Microbiol* 10:206; and Eckburg, P. B. et al. "Diversity of the human intestinal microbial flora." *Science* 308:1635-8 (2005)), but not older adults (Claesson, M. J. et al. "Composition, variability, and temporal stability of the intestinal microbiota of the elderly." *Proc. Natl. Acad. Sci. U.S.A.* 108 Suppl 1:4586-4591 (2011)). The abundance of Firmicutes sequences was substantially lower in CDI (43.2% vs. 74.9% in the healthy cohort; p=5.7×10$^{-7}$). This depletion in Firmicutes sequences was accompanied by a marked decrease in bacterial phylotypes (75 versus 322 phylotypes; p<8.17×10$^{-19}$; FIG. 3).

Figure 4A:
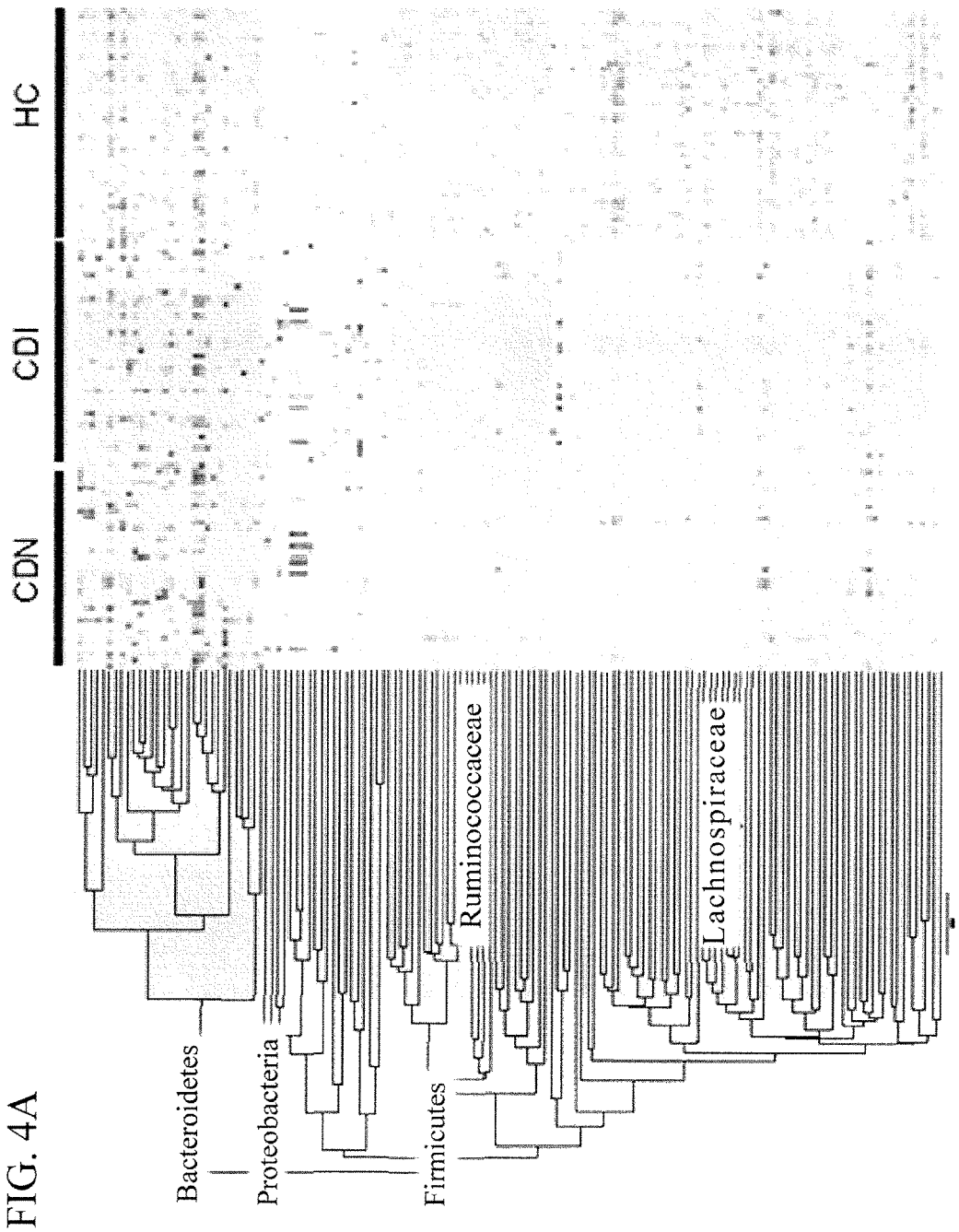
FIGS. 4A-4B show the proportion of bacterial taxa.
Figure 10:
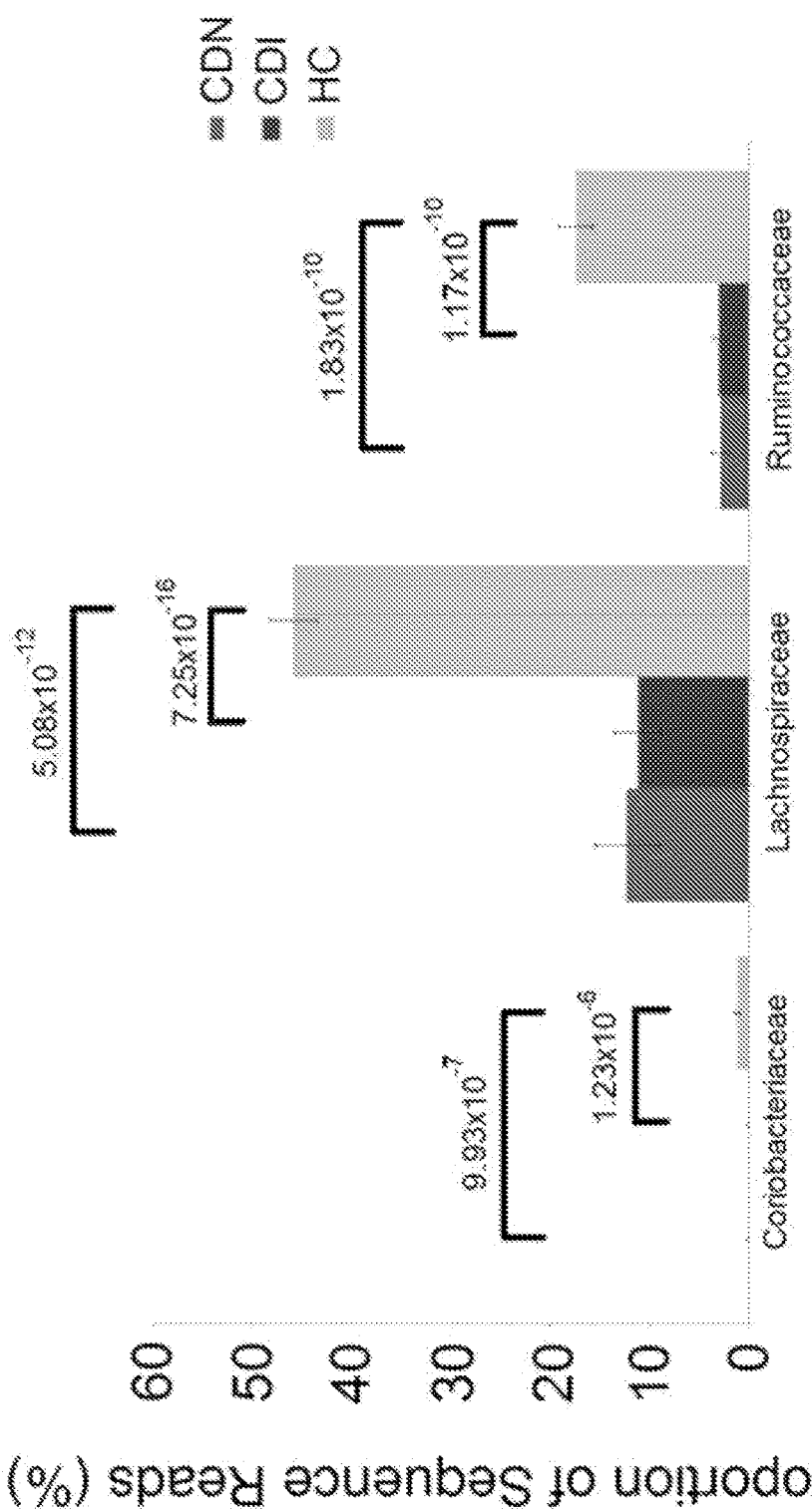
FIG. 10 is a graphical illustration of the paucity of Lachnospiraceae and Ruminococcaceae sequences in *C. difficile*-associated aggregate gut microbiota. The mean proportion of Lachnospiraceae and Ruminococcaceae sequences was lower in the CDI and CDN group (Student's t-test) compared to the healthy controls (HC).
Figure 11A:
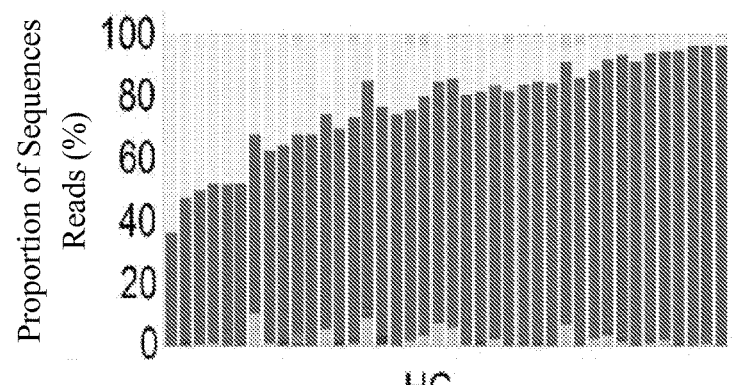
FIG. 11A-11C show interindividual variation in the proportion of major phyla. Subjects are ordered from left to right according to increasing proportions of Firmicutes reads.
Figure 11B:
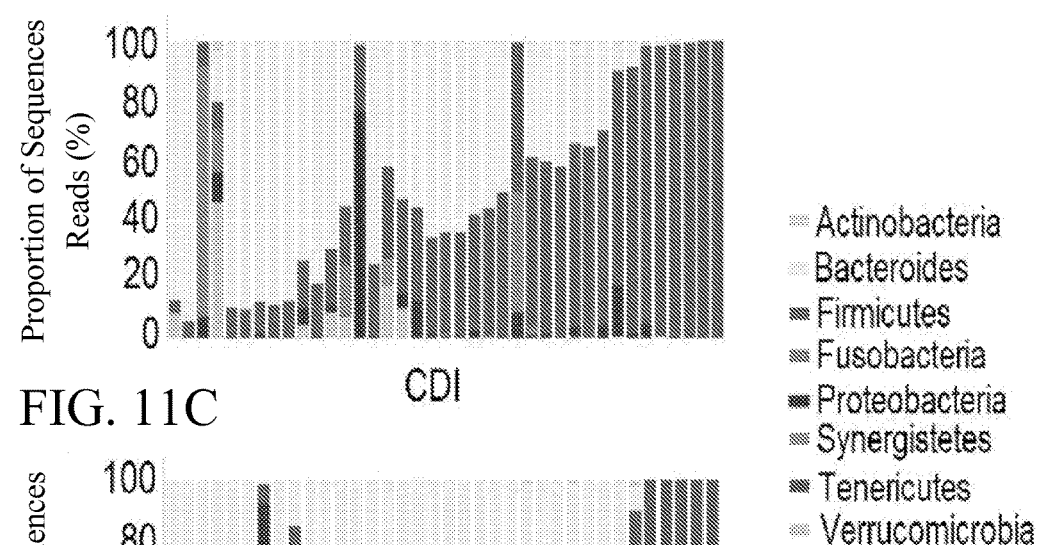
Figure 11C:
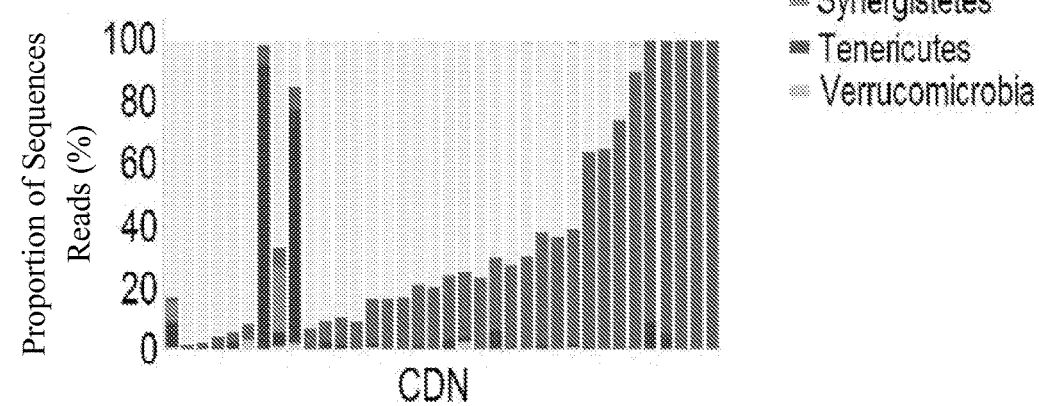
Figure 12A:
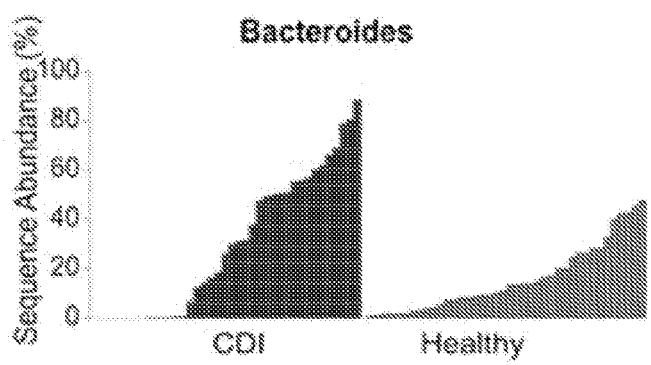
FIG. 12A-12D show interindividual variation in the proportion of sequence reads for the following genera.
Figure 12B:
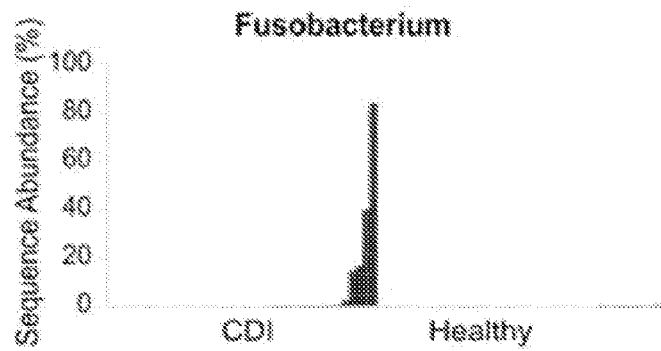
Figure 12C:
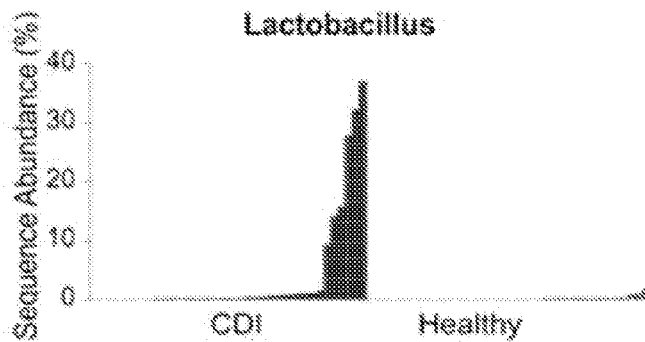
Figure 12D:
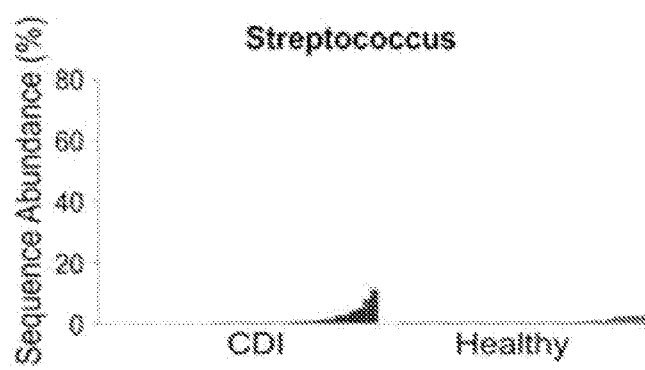

At the family level, Lachnospiraceae (45.8%), Ruminococcaceae (17.4%) and Bacteroidaceae (16.1%) sequences dominated the healthy fecal microbiota, and sequences from other families constituted <3% of all pyrosequence reads (FIG. 4A). Lachnospiraceae and Ruminococcaceae sequences were significantly underrepresented in CDI (11.2% vs. 45.8%; p=7.25×10$^{-16}$, and 3.0% vs. 17.4%; p=1.17×10$^{-10}$, respectively) (FIG. 10). In contrast, several genera were enriched in association with CDI. For example, *Veillonella* (4.5% versus 0.6%), *Enterococcus* (7.1% vs. 0.05%) and *Lactobacillus* (3.7% vs. 0.4%) sequences were unusually abundant. *Enterococcus* and *Lactobacillus* are both lactic acid bacteria from the order of Lactobacillales. *Enterococcus* sequences were found in 84.6% of the samples in CDI, compared to only 22.5% of the samples in healthy controls. Sequences from the Gammaproteobacteria class, which includes members of many clinically important gram-negative pathogens, were also enriched. Interestingly, Desulfovibrionaceae sequences from the Deltaproteobacteria class, which includes a large number of sulfate-reducing anaerobic gram-negative bacteria, were depleted in CDI. As in previous studies, considerable inter-individual variation in the proportion of major phyla among samples in all three groups was observed (Claesson, M. J. et al. "Composition, variability, and temporal stability of the intestinal microbiota of the elderly." *Proc. Natl. Acad. Sci. U.S.A.* 108 Suppl 1:4586-4591 (2011)) (FIG. 11). These results support the conclusion that decreased gut microbial diversity and richness associated with CDI is driven primarily by the loss of phylotypes within the Lachnospiraceae and Ruminococcaceae family.

Depletion of Butyrate-Producing Bacteria in CDI

Figure 4B:
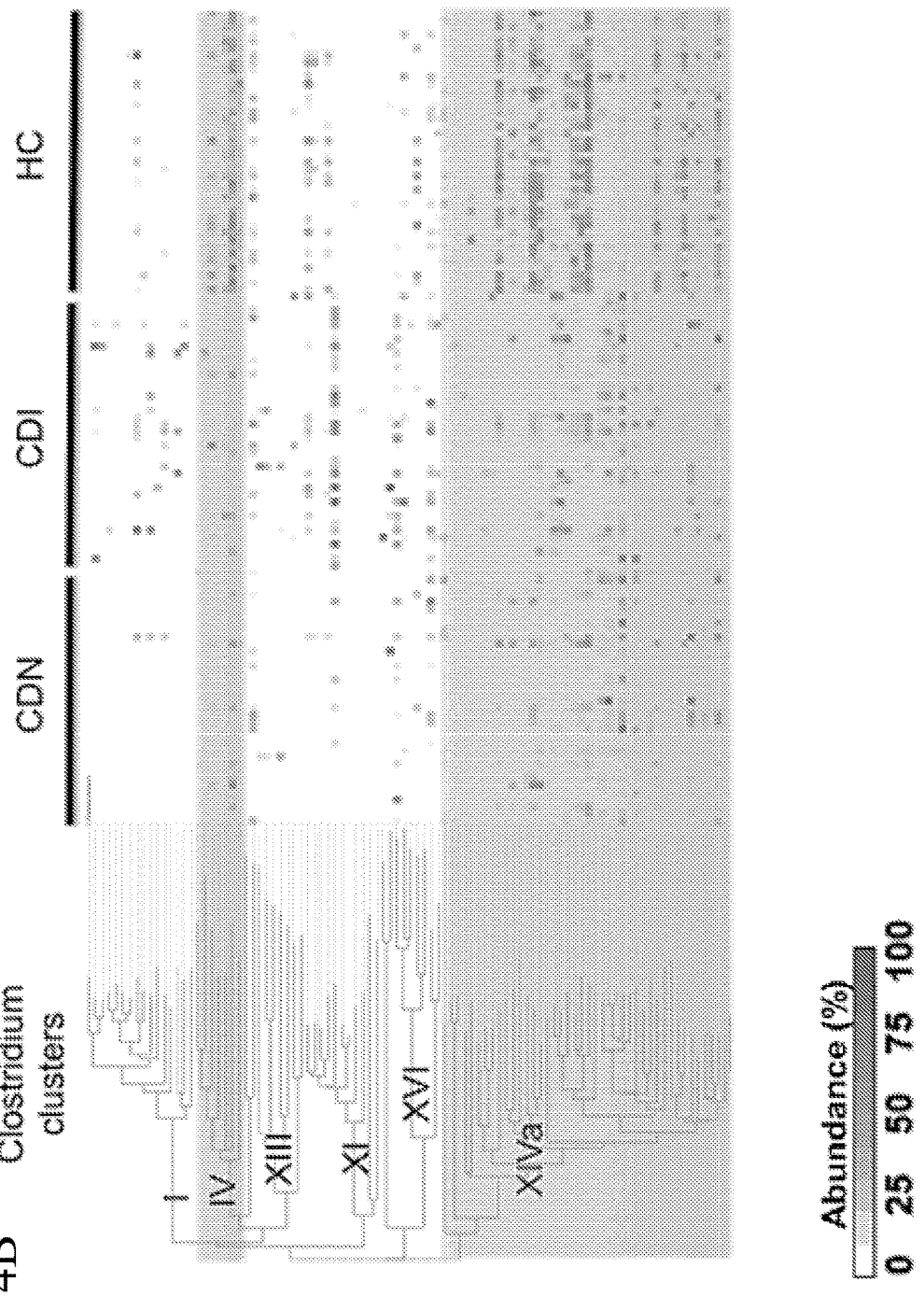

The vast majority of Firmicutes sequences (68.4%) were assigned to the Clostridia class. The clostridia class has been divided into 19 clusters on the basis of growth, metabolic, and morphologic parameters (Johnson, J. L., and Francis, B. S. 1975. Taxonomy of the Clostridia: ribosomal ribonucleic acid homologies among the species. *J. Gen. Microbiol.* 88:229-244.), and includes members of the Lachnospiraceae and Ruminococcaceae family that were significantly depleted in CDI. To identify specific *Clostridium* clusters most depleted in CDI, an association table of full-length sequences from species previously assigned to *Clostridium* clusters was used (Claesson, M. J. et al. 2011. Composition, variability, and temporal stability of the intestinal microbiota of the elderly. *Proc. Natl. Acad. Sci. U.S.A.* 108 Suppl 1:4586-4591; and Collins, M. D. et al. 1994. The phylogeny of the genus *Clostridium*: proposal of five new genera and eleven new species combinations. *Int. J. Syst. Bacteriol.* 44:812-826.), and assigned 17.8% of all reads to 19 *Clostridium* clusters (FIG. 4B). A lower proportion of reads was assigned for CDI (16.4%) compared to healthy controls (25.0%). Strikingly, members of the *Clostridium* cluster XIVa (the *Eubacterium rectale-Clostridium coccoides* group) and to a lesser extent Cluster IV (the *C. leptum* group) were significantly depleted in CDI compared to HC (Cluster XIVa: 5.5% vs 18.4%, p=5.1×10$^{-11}$; Cluster IV: 0.47% vs 2.95%, p=2.5×10$^{-7}$). Since *Clostridium* clusters IV and XIVa contain a large number of commensal organisms that include butyrate-producing anaerobic bacteria known to play an important role in colonic health, these data suggest a potential role for butyrate-producing organisms in *C. difficile* pathogenesis.

Figure 5A:
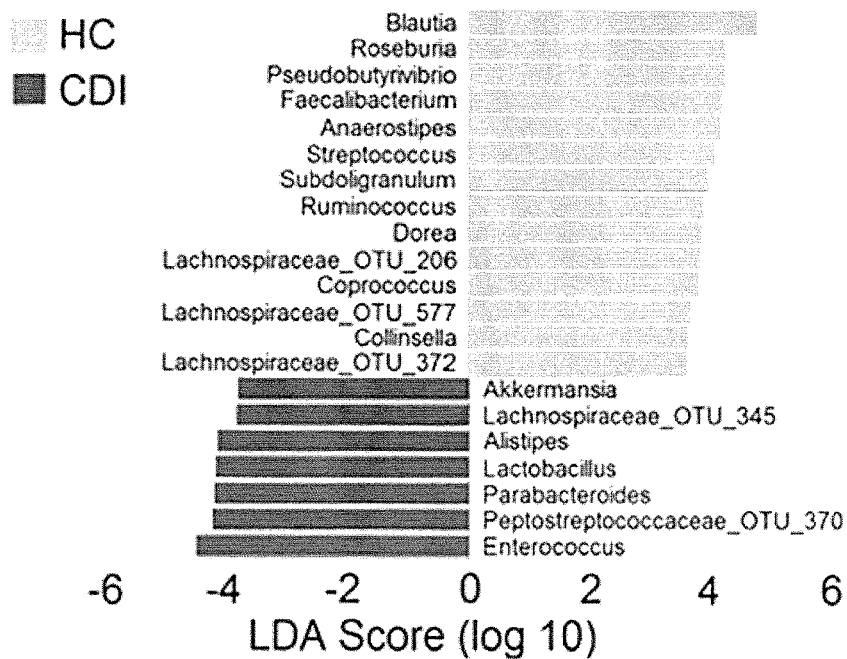
FIGS. 5A-5B show bacteria genera most depleted in CDI.
Figure 5B:
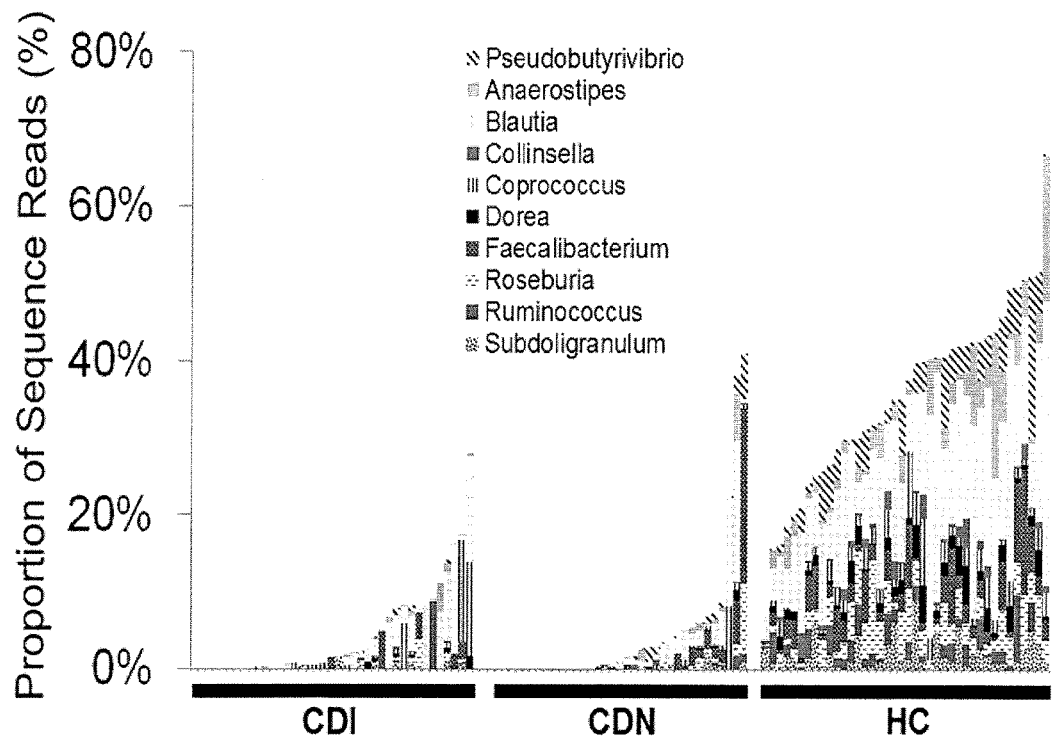

Next, LEfSe was used [linear discriminant analysis coupled with effect size measurements] (Segata, N. et al. 2011. Metagenomic biomarker discovery and explanation. Genome Biol. 12:R60.) to determine specific bacteria taxa that were differentially abundant. *Blautia, Pseudobutyrivibrio, Roseburia, Faecalibacterium, Anaerostipes, Subdoligranulum, Ruminococcus, Dorea,* and *Coprococcus* were identified as the most differentially depleted genera associated with CDI (FIG. 5A). Many of these are known butyrate producers belonging to *Clostridium* clusters IV or XIVa. Sequences from *Collinsella*, which belong to Coriobacteriaceae of the Actinobacteria phylum, were also depleted. The overall abundance of these 10 genera combined was significantly lower in CDI compared to controls (4.5% in CDI vs 35.6% in HC; p=4.0×10$^{-21}$), although inter-individual variations in the relative abundance of each genus were observed (FIG. 5B). Of the 3,531 total refOTUs identified in the dataset, 119 refOTUs were significantly depleted in CDI; 74 refOTUs were members of the 10 most depleted genera associated with CDI, and 39 refOTUs were uncultured bacteria in the Lachnospiraceae or Ruminococcaceae family.

Since butyrate producers affect colonic health by supplying energy to gut epithelial cells and are generally thought to play a protective role against colitis, further consideration was given regarding whether the abundance of 16S reads assigned to genera known to produce butyrate as their main fermentation products differed between CDI and the controls. The relative abundance of butyrate-producing bacteria was significantly lower in subjects with CDI (6.3% vs. 17.2% in healthy controls; p=0.0002; FIG. 6A). The major butyrate-producing bacteria that were depleted include *Roseburia* (0.17% vs, 3.4%, p=$3.2 \times 10^{-10}$), *Faecalibacterium* (0.37% vs. 3.2%, p=$5.4 \times 10^{-6}$), *Subdoligranulum* (0.18% vs. 2.0%, p=$1.8 \times 10^{-6}$), *Anaerostipes* (0.2% vs. 3.1%, p=0.0001), and *Pseudobutyrivibrio* (0.07% vs. 3.3%, p=$4.8 \times 10^{-6}$) (FIG. 6B). Interestingly, *Fusobacterium* spp. were the dominant butyrate-producers in the aggregate gut microbiota of subjects with CDI (4.1% vs. 0.03%, p=0.099), but this was driven by the dominance of *Fusobacterium* in the gut microbiota of four subjects (FIG. 12).

Anaerobic gut bacteria can produce a variety of fermentation products, including butyrate and also acetate, lactate and other short-chain fatty acids (SCFA). Comparison of major acetogens (FIG. 6C) revealed that the genera *Blautia* (2.1% vs. 14.4%, p=$3.7 \times 10^{-12}$) and *Dorea* (0.12% vs. 1.5%, p=$7.2 \times 10^{-8}$) were significantly depleted in CDI compared to controls. These acetogens were replaced in CDI by *Bacteroides* spp. (29.5% in CDI vs 16.1% in controls), which produces short-chain C2-C4 succinate, lactate, and formate, in addition to acetate. Interestingly, *Lactobacillus* spp. and *Enterococcus* spp., both primary lactic acid producers, were more prevalent and abundant in the gut microbiota of subjects with CDI (FIG. 6D and FIG. 12).

In this study, 16S genomic analysis of *C. difficile* associated gut microbiome revealed a profound alteration of gut microbiota, or dysbiosis, characterized by markedly decreased biodiversity and species richness. Importantly, this study identified a core set of normally abundant butyrate-producing anaerobic bacteria that are significantly depleted in CDI, implicating a potential role in *C. difficile* pathogenesis.

Specifically, this study identified several members of the Ruminococcaceae and Lachnospiraceae family that are markedly depleted in CDI. A great majority of these species are bacterial phylotypes with the greatest similarity to butyrate-producing anaerobic bacteria.

Figure 13:
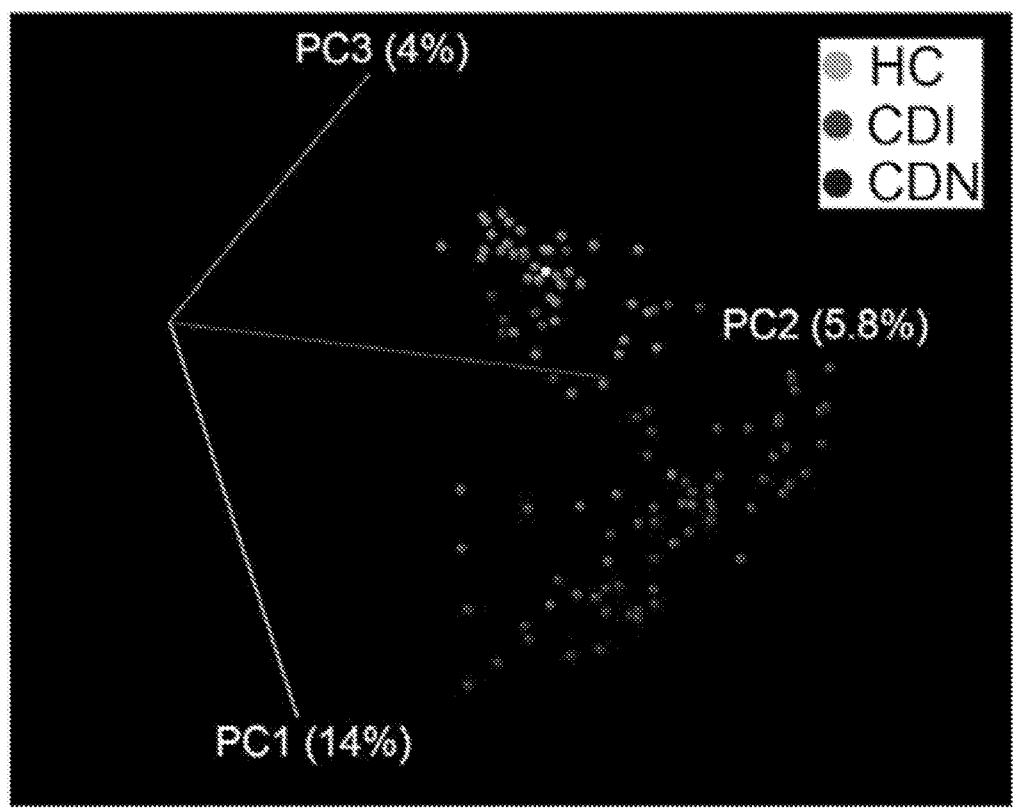
FIG. 13 shows unweighted UniFrac that was used to generate distances between *C. difficile*-positive fecal samples (CDI), *C. difficile*-negative diarrheal samples (CDN), and healthy controls (HC). Scatterplots were then generated using Principal Coordinate Analysis (PCoA). The percentage of variation explained by each PCoA is indicated on the axes. Each point represents a microbial community. The gut microbiota of the subject colonized with *C. difficile* clustered with the HC group.

Although the data provided above revealed considerable inter-individual variation in *C. difficile* associated gut microbiome, their microbial communities clustered separately and were clearly distinguishable from those of healthy individuals. These observations suggest a common pathway induced by antibiotics that leads to an altered, albeit somewhat variable, "susceptible" flora depleted in butyrate-producing bacteria. This "susceptible" flora may in turn predispose individuals to *C. difficile* infection. One hypothesis is that asymptomatic individuals colonized with *C. difficile* may harbor a diverse set of organisms with a more robust gut microbiota similar to that of a healthy individual. In support of this hypothesis, one of the healthy subjects in this study harbored *C. difficile* 16S pyrosequence reads and had positive toxin B PCR, thus indicating likely colonization with *C. difficile*. Analysis of this individual's gut microbiota revealed a large number of bacterial phylotypes with a complex microbial community structure that clustered with microbial communities from the healthy cohort (FIG. 13).

Example 2

Material and Methods:
Genomic DNA Isolation:

Genomic DNA (gDNA) was isolated using mechanical agitation coupled with a bead beating technique (Salonen, A., Nikkila, J., Jalanka-Tuovinen, J., Immonen, O., Rajilic-Stojanovic, M., Kekkonen, R. A., Palva, A., and de Vos, W. M. Comparative analysis of fecal DNA extraction methods with phylogenetic microarray: effective recovery of bacterial and archaeal DNA using mechanical cell lysis. *J Microbiol Methods* 81:127-34.). A sterile Q-tip applicator (Whittaker General Medical, Richmond, Va.) was applied to the stool sample and immersed in tubes containing 0.1 mm glass beads and lysis buffer (MO-BIO PowerSoil DNA Isolation kit, Carlsbad, Calif.). Tubes were immersed in a 95° C. water bath for 10 min before vortex/agitation according to manufacturer's recommendation. DNA was eluted in 50 µL elution buffer and concentrations were determined spectrophotometrically (Nanodrop 1000c, Thermo Scientific, Wilmington, Del.).

16S Barcoded PCR on Genomic DNA Template:

PCR was performed according to the National Institutes of Health Human Microbiome Project protocol. The V1-V3 16S rRNA region was amplified in a 20 µL reaction using 1 µL (not exceeding 100 ng) of template genomic DNA (gDNA) (or 1 µL of 1:10 diluted gDNA for concentrated sample), 0.75 U AccuPrime High Fidelity Taq DNA polymerase (Invitrogen, Carlsbad, Calif.), AccuPrime Buffer II (1.5 mM MgCl2, 0.2 mM of each dNTP), and 0.1 µM 534R reverse (with 454 Adaptor 'A') and 27F forward primers (with 454 Adaptor 'B'). The reverse primer (534R) also contained an 8-bp barcode unique to each sample which allowed for multiplex pyrosequencing.

The oligonucleotide sequence for the 534R primer was:

(SEQ ID NO: 1)
5'-CCATCTCATCCCTGCGTGTCTCCGACTCAG-

[8 bp barcode]-ATTACCGCGGCTGCTGG-3'

The sequence for the forward primer was:

(SEQ ID NO: 2)
5'CCTATCCCCTGTGTGCCTTGGCAGTCTCAGAGAGTTTGATCCTGGC

TCAG-3'

PCR reactions were performed in quadruplicate using the following cycling condition: (I) 95° C. for 2 minutes (hot start); (II) 95° C. for 20 seconds, 56° C. for 30 seconds and 72° C. for 5 minutes (30 cycles); (III) maintain at 4° C. PCR products were resolved on 1% agarose gel stained with SYBR Safe (Invitrogen, Carlsbad, Calif.). PCR fragments of ~500 bp were excised, and gel purified using the Qiagen gel extraction kit. The final barcoded PCR product was eluted in 32 µL of the elution buffer pre-heated to 55° C. and stored at −20° C. until pooling for pyrosequencing.

Amplicons were quantitated using a fluorometric assay (Qubit, Invitrogen, Carlsbad, Calif.) measured in triplicate, and pooled at equimolar concentrations for pyrosequencing at the University of Florida Interdisciplinary Center for Biotechnology Research (ICBR) using the Roche/454 GS-FLX platform with titanium based chemistry. Unidirectional sequencing was performed using the Library L reagents from adaptor side 'A'. From a single run (¾ of a picoTiter™ plate), 617,566 reads were obtained (Table 2). After quality control and filtering (see below) which required 100% match to the barcodes, 549,643 (89%) were available for downstream analysis. Sequences from all 115 samples were equally represented with an average of ~4,780 high quality reads per sample, and an average amplicon length of 492 base pairs after removal of primer, barcode, and 454 adapter sequences. Data for each pool are shown in FIG. 14.

PCR of *C. difficile* toxinB Gene:

Toxin B (tcdB) specific PCR (Alonso, R., Munoz, C., Gros, S., Garcia de Viedma, D., Pelaez, T., and Bouza, E. 1999. Rapid detection of toxigenic *Clostridium difficile* from stool samples by a nested PCR of toxin B gene. *J. Hosp.*

*Infect.* 41:145-149; Gumerlock, P. H., Tang, Y. J., Meyers, F. J., and Silva, J., Jr. 1991. Use of the polymerase chain reaction for the specific and direct detection of *Clostridium difficile* in human feces. *Rev. Infect. Dis.* 13:1053-1060; Kuhl, S. J., Tang, Y. J., Navarro, L., Gumerlock, P. H., and J., S., Jr. 1993. Diagnosis and monitoring of *Clostridium difficile* infections with the polymerase chain reaction. *Clin Infect Dis* 16 Suppl 4:S234-8; and Kato, N., Ou, C. Y., Kato, H., Bartley, S. L., Luo, C. C., Killgore, G. E., and Ueno, K. 1993. Detection of toxigenic *Clostridium difficile* in stool specimens by the polymerase chain reaction. *J Infect Dis* 167:455-8.) was performed for all 115 stool specimens using the following primers (2): CTDB1: 5'-GTGGCCCT-GAAGCATATG-3' (SEQ ID NO:3) (forward), and CTDB2: 5'-TCCTCTCTCTGAACTTCTTGC-3' (SEQ ID NO:4) (reverse). PCR amplification of tcdB was performed in 25 µL reactions in triplicate using 30 ng of gDNA template, 0.6 µM of forward and reverse primers and GoTaq HotStart Polymerase Master Mix containing 200 µM of each dNTP, 2 mM MgCl2 and GoTaq enzyme (Promega). The following cycling condition was used: (I) 95° C. for 5 minutes (hot start) (II) 94° C. for 45 seconds, 52° C. for 45 seconds, and 72° C. for 30 seconds [30 cycles] (III) final extension of 72° C. for 10 minutes and (IV) 4° C. hold. As expected, all 39 samples from the CDI group showed a strong amplification product of expected size of ~300 bp. Representative 300 bp fragments were excised, gel-purified, cloned and sequenced. All sequences were confirmed as *C. difficile* tcdB gene (position 1,821 to 2,106). Samples from 7 subjects in the CDN group and 1 subject in the healthy controls repeatedly showed distinct, albeit faint, tcdB amplification. The one subject from the healthy control group likely represents *C. difficile* colonization (FIG. 13). Analysis of the gut microbiota from this subject showed that a majority of reads (29.8%) clustered to the genus *Blautia*. Interestingly, our 16S deep sequencing data did not yield any reads that clustered with *Clostridium difficile*, suggesting a very low abundance of *C. difficile* in the gut microbiota.

Bioinformatics Analysis of 16S Sequence Reads: (FIG. 7)
Trimming and refOTU Generation:

Reads were removed from analysis if they did not conform to the following criteria: (1) >440 bp (prior to trimming of barcode and primer sequences), (2) 100% match to the barcode and primer sequences, (3) no ambiguous base pair calls, and (4) average per base quality score of 25. Reads were compared to the SILVA (Pruesse, E., Quast, C., Knittel, K., Fuchs, B. M., Ludwig, W., Peplies, J., and Glockner, F. O. 2007. SILVA: a comprehensive online resource for quality checked and aligned ribosomal RNA sequence data compatible with ARB. *Nucleic Acids Res* 35:7188-96.) 16S reference database v108 and were assigned a best match using >=97% identity criteria with at least 50% coverage in the alignment of the query.

Reads were then counted and de-replicated to unique reference sequence-based operational taxonomic units (refOTU) with taxonomic information. These were further collapsed at a 97% clustering threshold (using the UCLUST and scripts written in R) to account for redundancies in the database. Further analysis such as tree construction employed representative full length refOTU sequences. FIG. 7 illustrates a flow chart of the pipeline used to taxonomically classify 454 sequence reads. All sequence datasets have been deposited in the NCBI Sequence Read Archive (SRA).

Unifrac Principal Coordinate Analysis:

For PCoA analysis, sequences from two or more communities were first arrayed on a common phylogenetic tree using the multiple sequence alignment from PyNAST (with a greengenes template as guide) and tree construction algorithm from FastTree. The fraction of the branch length unique to each community was determined. UniFrac distances between all communities were then calculated, and the resulting distance matrix was used for Principal Coordinates Analysis, taking into account the community membership alone (unweighted UniFrac), or both the community membership and the relative abundance (weighted UniFrac).

Statistical Analysis

All statistical comparisons between taxa at different phylogenetic levels were calculated using an unpaired Student's t-test (Graphpad, La Jolla, Calif.) and Minitab v.15 at $\alpha<0.05$. Heat maps comparing the abundance of different taxa and *Clostridum* clusters were generated using R. Boxplots comparing microbial diversity, OTU numbers, and species evenness were generated using R. LEfSe (Segata, N., Izard, J., Waldron, L., Gevers, D., Miropolsky, L., Garrett, W. S., and Huttenhower, C. 2011. Metagenomic biomarker discovery and explanation. *Genome Biol.* 12:R60.) was used to determine specific genera and species that were differentially abundant or depleted between groups.

Figures 15D, 16:
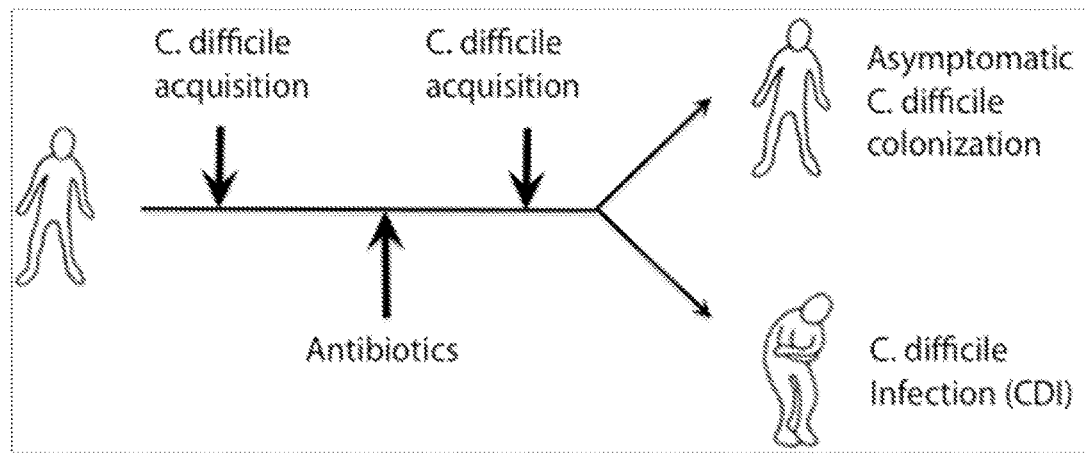
FIG. 16 is an illustration demonstrating the relationship between *Clostridium difficile* and antibiotic-associated diarrhea, where antibiotic-induced perturbation of gut microbiota is widely believed to provide *C. difficile* an undesirable advantage, allowing it to proliferate and elaborate its toxins in the background of a susceptible flora.
Figure 17:
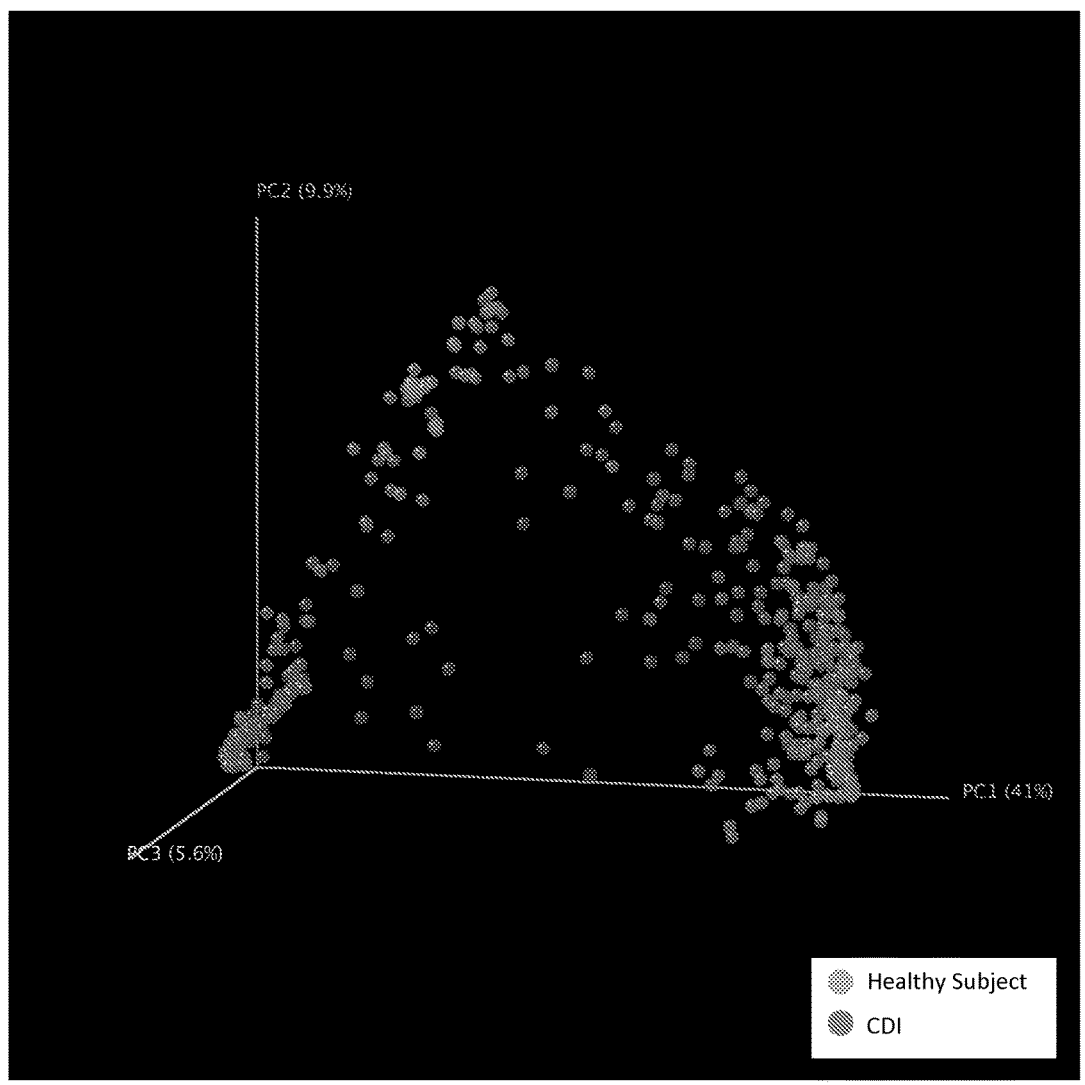
FIG. 17 is an illustration of the results from UniFrac analysis, using principal coordinates analysis (PCoA), demonstrating how gut microbial communities following CDI treatment undergo dramatic changes over time. Each point is a gut microbial community. Similar microbial communities cluster together using this analysis.
Figure 18A:
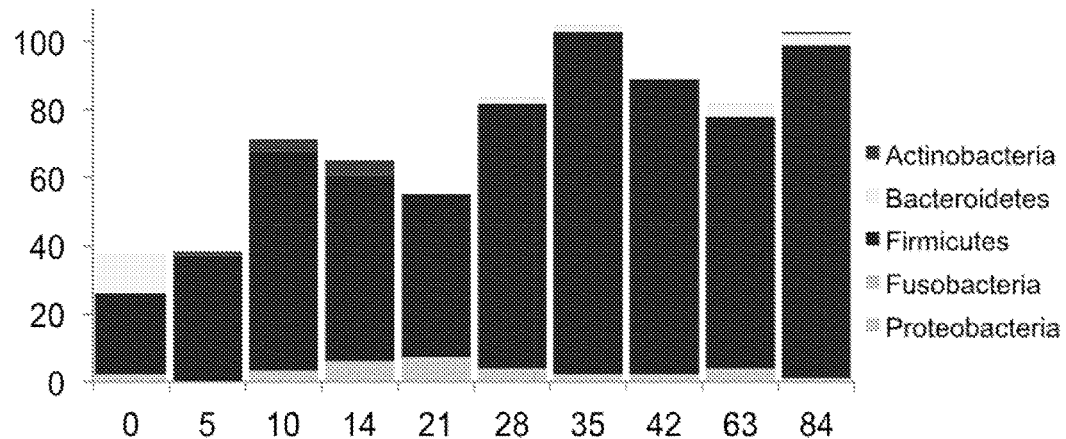
FIGS. 18A and 18B are graphical illustrations of "Cure" outcomes, defined as slow but steady recovery of Firmicutes phylotypes following *C. difficile* infection and treatment in a subject who was "cured.
Figure 18B:
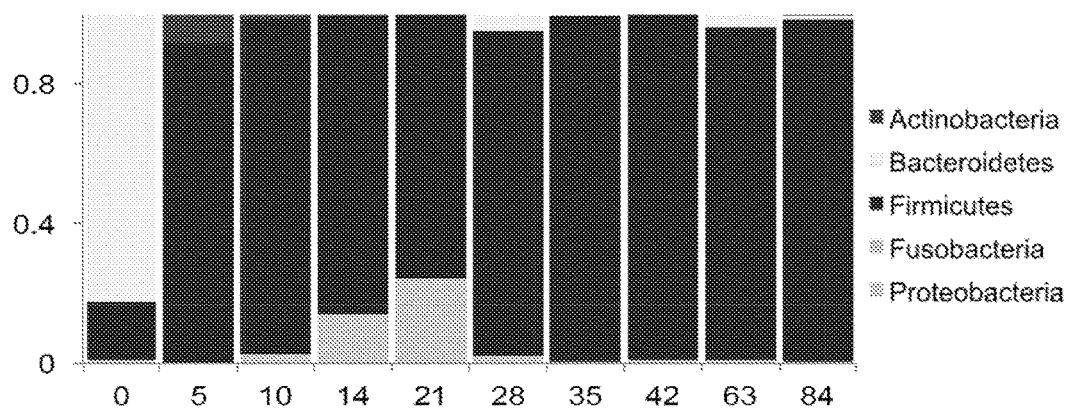
Figure 19A:
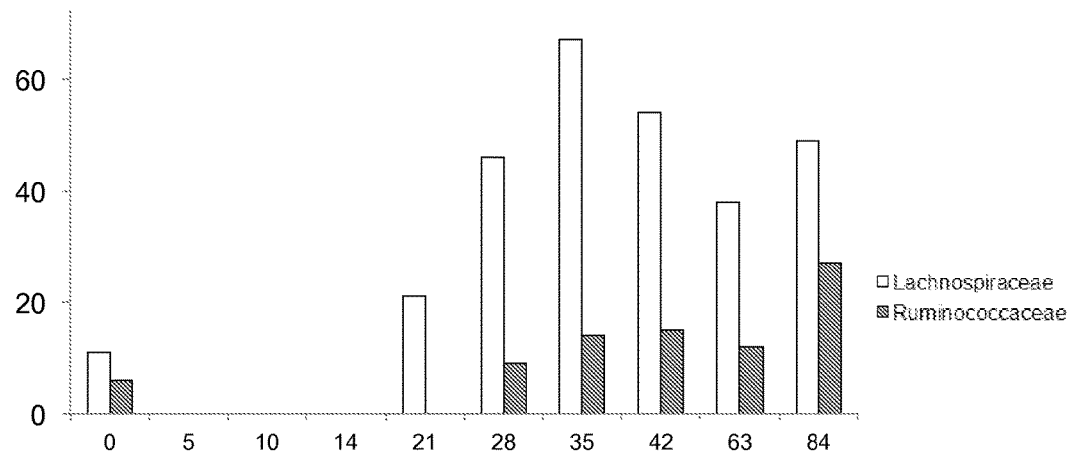
FIGS. 19A and 19B are graphical illustrations of the recovery of Lachnospiraceae and Ruminococcaceae is associated with "cure.
Figure 19B:
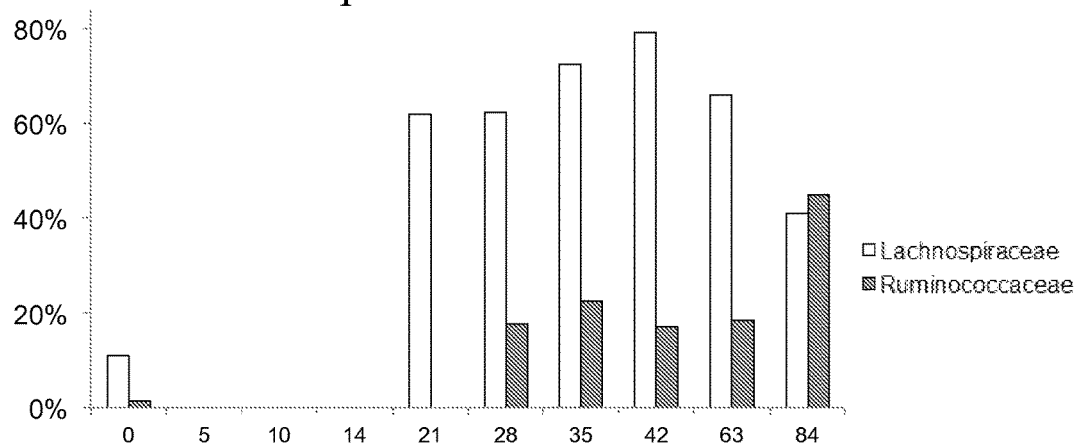
Figure 20A:
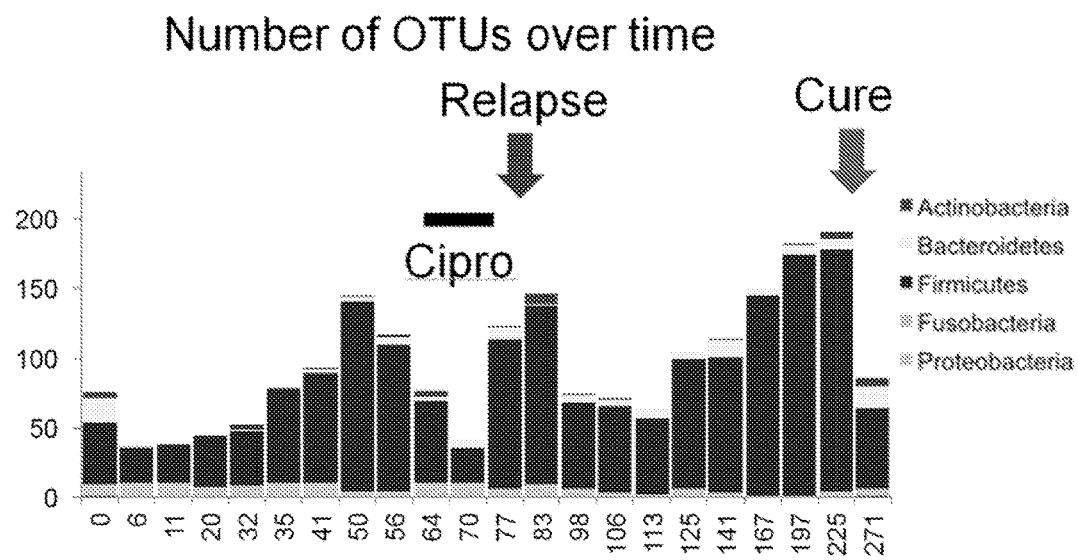
FIGS. 20A and 20B are graphical illustrations of the incomplete recovery of Firmicutes phylotypes prior to *C. difficile* relapse.
Figure 20B:
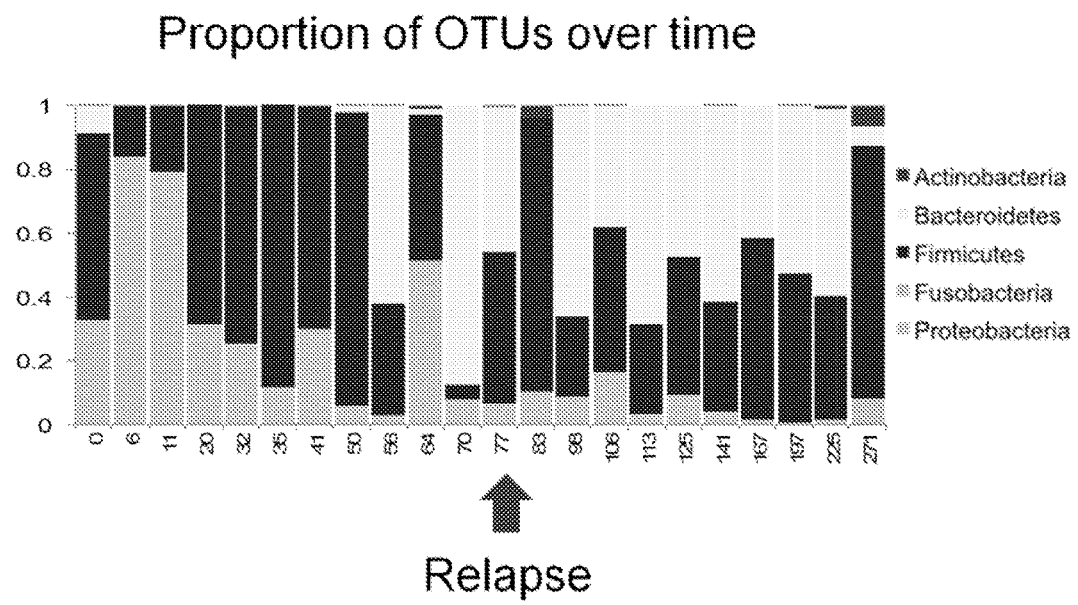

Metabolic Phenotypes:

137 major genera identified in our 16S deep sequencing data were classified according to their primary fermentation products as acetate, butyrate, lactate, or other producers (FIG. 15) using *Bergey's Manual of Systematic Bacteriology* (Bergey, D. H., Holt, J. G., and Krieg, N. R. 1984. Bergey's Manual of systematic bacteriology. 1st edition. Williams & Wilkins. Baltimore; Bergey, D. H., and Holt, J. G. 1994. *Bergey's manual of determinative bacteriology*. 9th edition. Williams & Wilkins. Baltimore. 787pp; and Boone, D. R., Castenholz, R. W., Garrity, G. M., and Bergey, D. H. 2001. *Bergey's manual of systematic bacteriology*. 2nd edition. Springer. N.Y.). For several genera, propionate was a co-product of fermentation, not their major product. Those genera that produce succinate, ethanol and H+ as their primary fermentative by-products were not included in the analysis shown in FIG. 6. The genera with unknown or ambiguous fermentative products were excluded—these were mostly genera with low abundance in our 16S dataset represented by <1% of the total reads.

Example 3

A longitudinal study was performed to assess whether a persistent depletion of Lachnospiraceae, Ruminococcaceae and butyrogenic bacteria is associated with recurrent *C. difficile* infection (CDI).

Methods

Samples of microbial communities in 494 longitudinal specimens from 30 adults following CDI up to 1 year were taken, and compared to fecal microbiota from 14 healthy controls. Genomic DNA was extracted from each specimen and the V1-V3 hypervariable region of bacterial 16S rRNA gene segments was amplified using broad-range rRNA PCR primers 27F and 534R and the amplicons were pooled and deep sequenced using Roche/454 pyrosequencing.

Results

With the pyrosequencing data analysis, a total of 494 longitudinal fecal samples from 30 subjects were analyzed by 16S pyrosequencing where an average of 3,986 sequence reads were obtained per sample. Roughly 2 million partial V1-V3 16S rRNA sequences from ~500 longitudinal fecal samples were analyzed, with identification of a total of 5,904 bacterial phylotypes. Phylogenetics-based analysis revealed that the gut microbiome undergoes a slow but steady recovery in microbial diversity and species richness over a period of a few months in response to *C. difficile* therapy. However, in patients who developed recurrent CDI, the recovery of gut microbial diversity and richness was slower and incomplete. There was a paucity of phylotypes within the Lachnospiraceae and Ruminococcaceae family in the Firmicutes Phylum prior to *C. difficile* recurrence (see Table 1). See also FIGS. 17, 18A, 18B, 19A, 19B, 20A, 20B, 21A and 21B.

TABLE 1

Subjects analyzed in the Study

| Outcome | % Subjects | Diarrheal Symptoms | *C. difficile* toxin B PCR |
|---|---|---|---|
| Cure | 44% | No | Negative |
| Colonized | 19% | No | Positive |
| Relapse | 30% | Yes | Positive |
| Insufficient Data | 7% | Unknown | N/A |

This study implicates members of the Lachnospiraceae and Ruminococcaceae family in the pathogenesis of recurrent *C. difficile* and suggests a potential role in colonization resistance against *C. difficile*. The organisms identified herein may lead to probiotic-based therapy for recurrent *C. difficile* and the development of a novel diagnostic test for predicting *C. difficile* recurrence.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A method for treating *Clostridium difficile* infection (CDI) comprising the step of administering to a mammal an effective amount of a composition comprising at least one strain of bacteria from the genus *Pseudobutryrivibrio* and, optionally, at least one other strain from the following butyrogenic bacterial genera: *Blautia, Roseburia, Dorea,* and *Coprococcus*.

2. The method of claim 1, wherein the composition comprises more than one strain of bacteria.

3. The method of claim 1, wherein the composition further comprises at least one strain from the following additional bacterial taxa: *Faecalibacterium, Anaerostipes, Subdoligranulum, Ruminoccocus, Streptococcus,* and *Lachnospiraceae*.

4. The method of claim 3, wherein the composition further comprises more than one additional strain of bacteria.

5. The method of claim 1, further comprising the step of diagnosing the CDI in the mammal.

6. The method of claim 1, further comprising the step of monitoring the CDI in the mammal.

* * * * *

SEQUENCE LISTING

```
<160> NUMBER OF SEQ ID NOS: 4

<210> SEQ ID NO 1
<211> LENGTH: 47
<212> TYPE: DNA
<213> ORGANISM: Artificial sequence
<220> FEATURE:
<223> OTHER INFORMATION: oligonucleotide sequence for the 534R primer

<400> SEQUENCE: 1
ccatctcatc cctgcgtgtc tccgactcag attaccgcgg ctgctgg                47

<210> SEQ ID NO 2
<211> LENGTH: 50
<212> TYPE: DNA
<213> ORGANISM: Artificial sequence
<220> FEATURE:
<223> OTHER INFORMATION: oligonucleotide sequence for the corresponding
      forward primer

<400> SEQUENCE: 2
cctatcccct gtgtgccttg gcagtctcag agagtttgat cctggctcag             50

<210> SEQ ID NO 3
<211> LENGTH: 18
<212> TYPE: DNA
<213> ORGANISM: Artificial sequence
<220> FEATURE:
<223> OTHER INFORMATION: forward primer CTDB1

<400> SEQUENCE: 3
gtggccctga agcatatg                                                18

<210> SEQ ID NO 4
<211> LENGTH: 21
<212> TYPE: DNA
<213> ORGANISM: Artificial sequence
<220> FEATURE:
<223> OTHER INFORMATION: reverse primer CTDB2

<400> SEQUENCE: 4
tcctctctct gaacttcttg c                                            21
```